(12) United States Patent
Yoon et al.

(10) Patent No.: US 10,751,377 B2
(45) Date of Patent: Aug. 25, 2020

(54) VIBRIO PARAHAEMOLYTICUS BACTERIOPHAGE VIB-PAP-1 AND USE THEREOF FOR INHIBITING PROLIFERATION OF VIBRIO PARAHAEMOLYTICUS

(71) Applicant: INTRON BIOTECHNOLOGY, INC., Gyeonggi-do (KR)

(72) Inventors: Seong Jun Yoon, Seoul (KR); Soo Youn Jun, Seoul (KR); An Sung Kwon, Gyeonggi-do (KR); Soon Hye Hwang, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 107 days.

(21) Appl. No.: 16/064,698

(22) PCT Filed: Nov. 10, 2016

(86) PCT No.: PCT/KR2016/012904
§ 371 (c)(1),
(2) Date: Jun. 21, 2018

(87) PCT Pub. No.: WO2017/111304
PCT Pub. Date: Jun. 29, 2017

(65) Prior Publication Data
US 2018/0369299 A1    Dec. 27, 2018

(30) Foreign Application Priority Data

Dec. 21, 2015 (KR) ........................ 10-2015-0182590

(51) Int. Cl.
*A61K 35/76* (2015.01)
*A23K 20/195* (2016.01)
*A23K 50/80* (2016.01)
*A61P 31/04* (2006.01)
*C12N 7/00* (2006.01)

(52) U.S. Cl.
CPC ............ *A61K 35/76* (2013.01); *A23K 20/195* (2016.05); *A23K 50/80* (2016.05); *A61P 31/04* (2018.01); *C12N 7/00* (2013.01); *C12N 2795/10221* (2013.01); *C12N 2795/10232* (2013.01)

(58) Field of Classification Search
None
See application file for complete search history.

(56) References Cited

FOREIGN PATENT DOCUMENTS

| KR | 10-2013-0021677 A | 3/2013 |
| KR | 10-1267616 B1 | 5/2013 |
| KR | 10-2014-0000541 A | 1/2014 |
| KR | 10-2015-0024115 A | 3/2015 |

OTHER PUBLICATIONS

Bastías, R. et al., A New Group of Cosmopolitan Bacteriophages Induce a Carrier State in the Pandemic Strain of *Vibrio paraharmolyticus*. Environ Microbiol. 2010; 12(4):990-1000.
NCBI, Genbank Accession No. FJ896200.1. 2010 (21 pages).
International Search Report dated Jan. 13, 2017 by the International Searching Authority for Patent Application No. PCT/KR2016/012904, which was filed on Nov. 10, 2016 and published as WO 2017/111304 on Jun. 29, 2017 (Inventor—Yoon et al.; Applicant—Intron Biotechnology, Inc.) (Original—4 pages; Translation: 2 pages).
International Search Report dated Feb. 20, 2017 by the International Searching Authority for Patent Application No. PCT/KR2016/012905, which was filed on Nov. 10, 2016 and published as WO 2017/111305 on Jun. 29, 2017 (Inventor—Yoon et al.; Applicant—Intron Biotechnology, Inc.) (Original—4 pages; Translation—2 pages).

*Primary Examiner* — Nicole Kinsey White
(74) *Attorney, Agent, or Firm* — Ballard Spahr LLP

(57) ABSTRACT

The present invention relates to: Podoviridae bacteriophage Vib-PAP-1 (accession number KCTC 12817BP) which has the capability to specifically destroy *Vibrio parahaemolyticus*, is characterized by having a genome represented by SEQ ID NO: 1, and is isolated from nature; and a method for preventing and treating *Vibrio parahaemolyticus* infections, using a composition containing bacteriophage Vib-PAP-1 as an active ingredient.

2 Claims, 2 Drawing Sheets
Specification includes a Sequence Listing.

[FIG. 1]
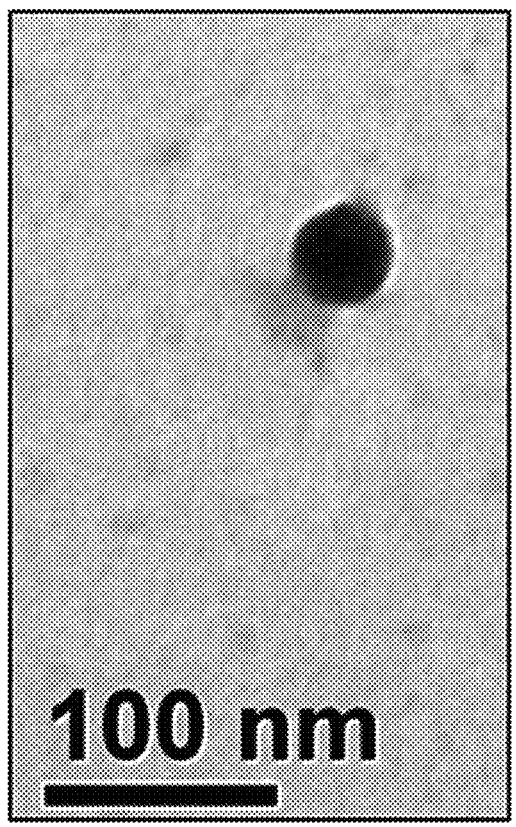

[FIG. 2]
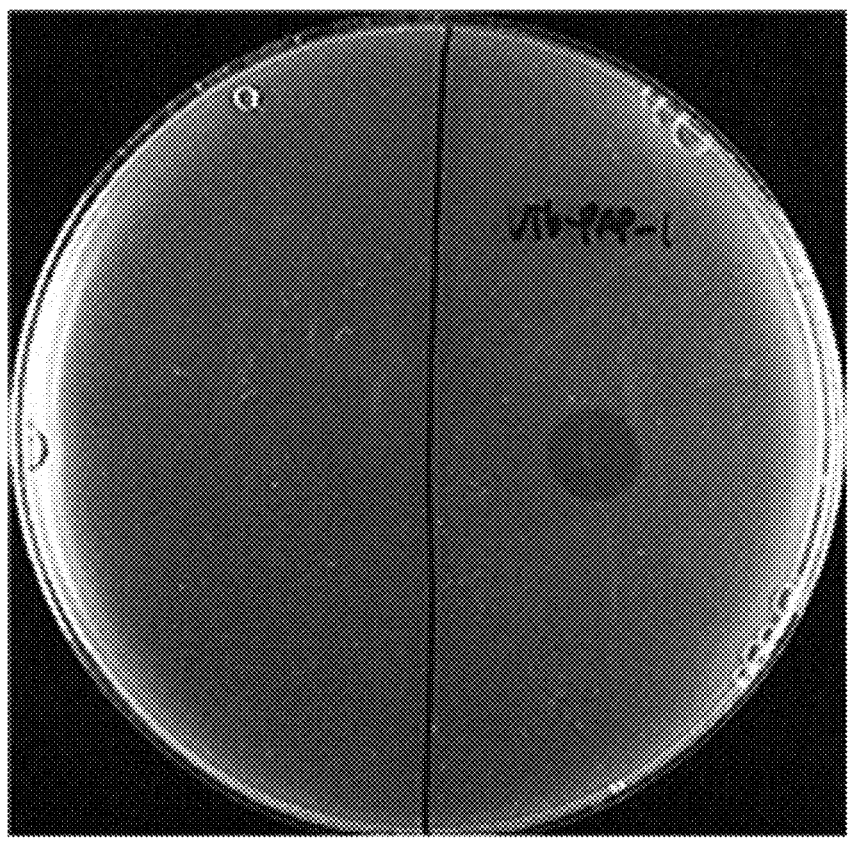

US 10,751,377 B2

SEQUENCE LISTING

<160> NUMBER OF SEQ ID NOS: 1

<210> SEQ ID NO 1
<211> LENGTH: 42808
<212> TYPE: DNA
<213> ORGANISM: Vibrio parahaemolyticus
<220> FEATURE:
<221> NAME/KEY: misc_feature
<222> LOCATION: (1)..(42808)
<223> OTHER INFORMATION: Vibrio parahaemolyticus bacteriophage Vib-PAP-1

<400> SEQUENCE: 1

```
gtacaaccat cgacatttac gatgcggcta gtgatatgat gtacggtgag aatgaagatg      60
gtttgctact ggattacgcc accaataaca ttgtattcaa cgagtccaag ctattgcgta     120
tcgtgtttga tataccgttc gaacacatgc cagaaatggc gcaacaaatc gtcgcatacg     180
aggcggctat gcaagtttat gcgaatgacc taggtgtgga caaccagtac cagaacttag     240
accgtcaggc gcaagaggcg ttccgggtgc tgcataagca gaacctacgt aaccgccgct     300
acagtacaag caagacaggg cgttaccgtc gtatccgctc tgcactacat acatagaggt     360
gaatcatggc tcgaccattt gagggtgcat gaatgacct gctgcaaggt gtgtcccaac      420
aagttccacg tgagcgtgtg gctggacaat gctcggcaca ggttaacatg ctgtccgacc     480
cagtaacagg catccgtcgt cgtcccggta gtctgttcgt gagtgtgcac gatttcggcc     540
cgattggtga gggtgacgca ctgtacacgc agtatctcga acgaggtgct gatggacgac     600
acttagtaat caacaccaac acaggcggtt ggtggctctt agaccgtgag gctaagaaca     660
tcgtgagtga gggtaactta tcgtacctcc tagcggctga ccgtcgcagt atccagacta     720
ccagtatggg cggtgtcacg tacattctga atactgagaa gcgcccgtct gcaacgactg     780
acaactctga caagaaagac ccgaagacaa ctggtttcta ctttgtcaag agtggtgcgt     840
tcagtaaaga gtacgatatt tccgtagtgt ggtctgaggg tagccagact gtaacatata     900
ccacacctga tggtacaacc gcaggtgacg cagaccaatc tgtaccggaa gcaatcgcgc     960
gtaaacttgt ggaggaatta attgcagtag gtgtggactt cgctgtgcgc gttggcccgt    1020
acatttactt cgaactaatc acaggtactg accttaaaat cacaagtacg tctggttcgc    1080
cttacattgg ttactcaaac caatcacagg taaacctaga gactgacctc cctgcgcgtc    1140
tgcatccgtc tgctgatggt gcgttgtgtg ccgtaggtca atcagaacgt gctcttgtgt    1200
ggtatcgtta cagttccgaa aagggtgtat ggctagaatc tggtgactac aactctgtga    1260
ccgctattag tgtggatgtg ccttataaga ttgtcgatga caatatggag caacatatca    1320
tggaggggcg tctcgcaggt gacgacttaa ctaaccctgc accgacattc cttgaggaac    1380
gccgcatcac tggtatcggt acgttccaag gtcgcttagt gcttctgtcc ggtgcgtacg    1440
tctgtatgag tgccactggc gaaccagacc gcttcttccg ctctaccgtg agttcccttg    1500
acccaacaga ccgtattgat attgcatccg gttcggcaca gaactcagtg ttccgccaag    1560
cattgcagtt caacaaggac ttgatttac ttggtgatag tacacaggcg gtagtaccgt    1620
ccctacaaca gctacttgcg cctgataatg caagcgtggt gttaacctca gatttggcct    1680
gtaatgcgtt tgtagcacct gttacaacct cgcagaccct gatgtaccct gcacctcgaa    1740
gcgaagcgtt cagtgcagtt ctggagcttg ttccgtcgca attcacatcg tctcagtacg    1800
tatctcaaga cgttacgacg cacatccccc gttacatcga gggtgaggcg cgtttcatgc    1860
agagtgcgag tgctgcgaac atcgtgctaa tgcaactac tggggacaac cgtcaagtgg    1920
ttgcacatga ataccacttc acaagtcaag gtaaagtgca ccaagcatgg cacaaatggg    1980
```

```
tgttcccgta ccgtgtcgct agtctacact ttgcgcgtga ccgtgttgtg ctgtttgccg    2040
cagatgatgc tggtagtacg gataaaatca ctatctcgac catcgaccct aagcagggtg    2100
gtgtgacgtt taatgttgac cgcctaccac acctagattc gatgagcctt gtgcctgtta    2160
gtgatggtaa gggcatcgtg ccaatctaca tgcgtccgtg ggtatctgag ggtaagttgg    2220
ctggctctgt tgctacaggt gcattagcgt ctgaggaagt ggctattgat gtggacgagg    2280
tttcgtggga attcactgta gagccgggtt tcaaagactc gcaaatctac ttaggcttcc    2340
gctacgaatc gttgtttgcg cctacgccac ctatgctgaa agaccagaac gacacattaa    2400
tcagtactgc tccggttcgg ctgttgcgtt atgagttgac aacccgaaat acaggtgaat    2460
tcgatgtacg catcgttgac cctactattg ggctagacta ctcagacagt gcaaccagcc    2520
tagtgtttgg tactgacagt gtgcagttga accaagcctt agtgtctgac ttggcacgtg    2580
tccctgtacc gtgtcgaagt aatgcacagt ccactgaaat gtacttgagt actgatggta    2640
cacaggatat gaacattctg gaaattgaat atatcattcg ttacaaccaa cgccgacgtc    2700
gcgtataagg agttaatatg gcaggtgcaa gtggtggcgg tgtcgccact ggtgctgcgt    2760
ctggtgctgc tgctggtgca tccattggtg gcccttgggg tgcagctatt ggtgctgtag    2820
taggcgcggc gtcagcattg ttcactggta gtcaagcagc taaggcggag aacaaagccg    2880
ccgtagcgcg aaatcaggct atcatggagt acaacaagaa agtcatgctt agcacagctc    2940
agtctgtgtc gcagattaac ttgcaacgct ctattgagaa ccagaagacc gccagtgcac    3000
tattcaacat caacgcacag aagaacgccg ctgctaacca aactcgtgct atggctgctg    3060
ccacagacac tgttggcgtt agtgcgcgtg atgctgcgca atccgtcatg gtcaacgctg    3120
accgtgctca aggtcagtt gagaaccaac acgtaatcac gaacgagggt ttcaacatga    3180
tgttacgtaa gactaccgac gagggcagca atgctctgca aggtggtgta gcatcatccg    3240
gtgaacaaat catgaacgct gcatacgggc aggctgctgg tatcatggtg ggtgctgctg    3300
cggactacgg tttcagccag ttaacaccac aaaaccagac acagccaaaa gaagtcccaa    3360
gtgcaggaaa gaatgacgct gattacgatt ggtggggacg tagcgccttt aaccaaattg    3420
accttaattt cagttattcg gatacaccaa taactacaag ttggtaagga gataatatgc    3480
caatccaaag caatccgcta caactcggag ctgcaactgg caacctgttg attggtgcgg    3540
cctctccacg tatggagaac gtacaggctg agcctgacgc aagtggtgcg ctgattgctg    3600
gattcctgca aacagccgtg ccagcagtgg agcgtgcgta caatcaagcc gcagccgatg    3660
cagcaattca aggtgcacta gacgccactg ccacgactga cgccatgagc aagcaagatg    3720
aaaagctcag caaggtgaac atgctattca aggagtccta ccaatcgggc tacttgagcg    3780
cagcagtgaa tcaggaaatg ggcaagttcc gtcaggagca aatcgaccaa atcaataacg    3840
ccgtatctca gggtatggac ttggaggact cgataagct gagccaagag cgtaatgctg    3900
cgttcgccag ccagatgagt aagtacctcc ctcacatccc taagcaatcg gcaatggcac    3960
tattgcaaga cctacaggaa acgtctgtag cggctcgtaa caagttccag aaagactccg    4020
ctgcaatggc tactgtagct gctgaccgcg cgttagacag caacctagat ggcacagcga    4080
cggagttcta cagctttgtg gattccggtg caccagaaat ggcacaggct agtattgcga    4140
aaggtcttcg cagcattaac ctgtctacgc acttgtcaaa ggatgacaaa atccaacgtg    4200
ctaaggcgta cgtgcagaca gtcgcacagc gcactgatga gccaagtgtt atcaacatgc    4260
tgcaaggtgt ggttgataag gaaatgggtg tgttaagccc gacggttatc aaggcgttac    4320
```

```
gcactgagta caaccgcgca ggaaaccagc aagctgctca ggctatggtg agtttcgaaa    4380
cggacatcaa cggtctaacc tcactaccac cggatgaaca agcgtctgag cttacacgcc    4440
tacgtaactt cgtggatgat aaggcgcagc aaggtatcat cgaggctggt actgctggcg    4500
cgtacgtgaa gcgtttgaac gaggcagaga agaaagcgcg tcaagcgaac acttttgaac    4560
ttgcactgaa caacgctatc ccgtcaactg tcctagctgg tcagctcggt atggacttag    4620
acaagactcg taaagagtta gagaagaact cccagacac tgctcaaggt aacttggcaa    4680
tgatggcata tgcttcaaag gctaatgact cgtacatggc ttcccttgcg gctaaacgta    4740
tgagtacgaa cactggtcag gtcttagcga caatcgactt cacaggcaag gataacgtcg    4800
tcagtgagga acaacaggcg caggttgctt catgggtgat gatgtacaac cagagcactg    4860
acattggtaa gcagacgatg ctacagagcc taccggagaa cctacgcggc ccgatgggta    4920
acgctgcatt acagaacccg gagaacgcga gtaacatcct gttcgatgac ctgcgacgca    4980
atgctcaggc tattgcttct ggcaagtaca acgcgcagaa tgcaacgatg cctaatgact    5040
tgattgatgg tacgaagctg aacaactggc ttgacttcgg cacagagagt gaccgtcagg    5100
tgactgctgg tgctactgct gtggcacaga gctggaagta cattgcacag aaacgcccag    5160
aactgactaa cgacttgggt gctatggaga agctgcttta gcagatgcc agcacacgta    5220 aagtagaatt acaggtaggt ggggagaaca tccacacgta cgttcctgtc ggtaagacat    5280
tagagaactt cttcggtgac tacaagggtg ataagtcttt ctttgtcaag gctatgaaca    5340
accaagtgga atccgtactg tctagcgtta agactgatgt tagtggggta tctgtggaca    5400
ttggtgcagc aggtggtgac gctatgggta tggtggtagc cgtggaggac tctgatggta    5460
ttgtgacgcg ttacagtatc cccggtagta ctctacaaca ggctgcgacc actatcaaca    5520
aggatgcgat taagactgcc gcaggtctgg gtgctcaaca aagtggccta accactgcta    5580
cgttctatga tgcaacgaat aaccgcgctg taactatgaa cgtgactggt gtgaacaagt    5640
caggcattga cccattcgtg ttcggtaagt taaccgctaa cctgatggaa tctgagggct    5700
tccttggcaa gaagaagaaa gcaggtggtg gtgagactgt gggctttgga cgccacacta    5760
attccggtaa ggctattgat gacgaggtga cactcccaca agctatcggt atgctcaagg    5820
gcgacctaga agatacgtac atcccaatgg ttaagtcagc ggctaagtct gctggtcttg    5880
agttgagcga tgctgcatat cctgtactgg ttgaccttgc gtatcatggt ggcggtggta    5940
gcgcgaaccc tgtggctaag gctatggcgg attacgctaa gggtgtgaac caattcgaca    6000
acctaactaa ccgcatgtta gtgatgaaca ctatgatgca gacccctgcg tacaagcaat    6060
caggaaagac tcgacaagag caattacgta ctgacttgac aagttggctt caacagaacc    6120
aacctgctaa gaatccgtac ccaacctatt actaagtggt ggggcatttg ccctcccctt    6180
atcattacac tttgaggaac tttatggct attttcaga accgtcgccc atcttcacag    6240
ggtgctggct tagagtctaa tgctaagggc gtgaacggcg cagacatgga cgctggtgcg    6300
ctggcatggg aagacactac tgacttaggt ttaaacgctg cggagcgtga ggcgaacctt    6360
aaacgccttg aaacaccgaa agcaactgga ctcgaatcat tcgcagcagg tgttggtaac    6420
agcatcgtag gtgcggctgt gcgcaaagca acgatgccag acttcccaga ggacacatcc    6480
tttgaccttg gtactactat gacagcagac acctctctgc gcattctagg gtactcagaa    6540
gaagaattga acttcattgg tggctcacgt agccttgatg agtaccagta ccgtaaagag    6600
gctgtggaag accaacgcaa gcgtgatggt gtacaagcag agaatatgtt tgcaggtatc    6660
gctggtaact tagcaggtga cgcaccgttc ctacttgccc ctatgggtgc agcaggtgta    6720
```

```
gcaggtcgta ctggtatggc tgtgcgtgct gcgctgcgtg ctggcgagtt agcgactact    6780
tactacgccc aagaccaact aggtcaggct gaatgggtta cagcggttgc cgcaggttta    6840
atcggtgttg accaactgta cgacgtatca cgtgcaactc gcggtgtgcg cgcagcagcg    6900
aatgcagcag aagttgagag ccgcgcttta ggctctgcga ctgagcatgt gttcaccgct    6960
gagacaggtt tagcacgcaa agcacagact ggtggtgtac taagtgacgc tccagaaatc    7020
gtgcctgatg tggtaaaacc agaggtcgct gcacagcgaa tgcctgaccc tgatgcacct    7080
gtaaatgaag ttccagaggt ggtaaaagtc ccacgtacag gtaaggggga acgaagtttc    7140
ccattacagg acacacctgt tgagggtcga attgttgcct ctcgacaagg acgtaagaca    7200
gttcaaatta agcacaaga cttagtgaca cacctccgta ctatggatag tttgtcagac    7260
tcagcccgtg ctcttatgga cgcactgcca gatactattt ctggtatgga ggtgcgttta    7320
atgaatgcta ctggtcgtcg ctcatcctac acctttggtg ctaacactga gtttctgaaa    7380
ctacgctcta cagcgaaaga cggtacagtg tttaaaaccg tgggcgatat gttgaaccac    7440
gtagatgcag acgttgctgt gcatgagctt attcatgctg cgacatcgaa gactttattc    7500
caagcaagta aaggtaacgt tgctcctgag attgcagatg ctatccgtga ccttgatgct    7560
ttacatgcct cactgaaaaa caatcgtgag ttcgctcgta agtacagcta cgctatgact    7620
aacaatcgtg agttcctagc agagttggcg tctaaaccgg aaatggtgaa agacctagcg    7680
aagttaccgg gtgtccgtgc aggtcagaat gctttgcaag ctgtggctga aagattctg    7740 aaaatgttag gcttcaaagg cacaggctca gctcttgatg aagcggttga tgcctttgtt    7800
aaggttgcta actaccaagc tgataaccta gacaaagtga atgctttctt ctctgatggt    7860
atggctgacc ttgcagacga cgcaaaccgt ggtgctactg cggttgagcg tgctaaacgt    7920
cttgagcaag gtgtccgtaa atctttgaag cagtcgttcg cactctggga caacatcgct    7980
cgtggtagtg aagacctagc gaacctactt gtatctgatg ctacccgtat gggtgaacgt    8040
gctaccagtg tggtagacca taaacgtaac ttgactcttg agcagaacct acgtgctgcc    8100
gctgttgagg atgcaattgt ggctgctatg cgtgagaagc atggcgttaa caccttttgat    8160 atgttctttta accgtgctaa ggctcgtaca gcccgtagtg tggaagaaga caaactgact    8220
aagtatctgc atgaagcata cagtgctgag aaagcagggc gtgaaatccc aacaccacca    8280
gccgacattg agcgtttggt gaaagcctac accgattccg gttgggctga gtcttggcat    8340
gagcaccttg tgaaatccgg tactatcagt gcagacgagt tcccacgctc gaagtactac    8400
atcccccgtc aatacagcta cgagaaagtg cgtaacatcg aaccgcctaa agttaagaaa    8460
ctgctacgct ctgcgttgca agatacttac actaacatgg atggtaagct ggctgcgcgt    8520
gtcgctgact cttggtacaa ccgcatcgtg aatggtgtat ccggtaacgg tggcccacaa    8580
tggaagaact tgatgcaagg tatggataac gatgagttgt tcatggctct gcgtgatgct    8640
ggagttgaag acgacaaaat caacgagttc tacgtgtgga acgtaccgaa gacaggtagc    8700
actgctccag tgaagaactt gcgtaaccgc cttgacttga acttgaacaa agagttcgac    8760
attgatggtg atgtgctacg tttatctgac atcctagaga ctaacacact tggcttgatg    8820
caaggttaca caaaccgcat gtcaggtcgt gtggcgtttg cgaatcgtgg tatcactgat    8880
ttacgtgcac ttgaccgttc aatcactgag actcgactag gtatgggtga gggtgcagaa    8940
tcatggggca aagcagtgga tgacacaatc gaccacctgc taggctaccc agtcggtact    9000
gacatccctg agctgatgcg tggtgcaagc aaccttgcta acactgtgat gctaaagaac    9060
```

```
tccggtttat accagatgac tgacattagt atcgcaatga aagagttcgg tttagctcgt    9120
gtactacgtg gtttagcaag tactggtctg ttacgtaagg ctgacgcagt tgttgcggat    9180
actggctctc gtgagcgtct gtacagcatc ttgaatggcg cgtaccagaa cgaagcacga    9240
taccgtcaca tccacacata cgctgacgat aaccttgact tgacaaacac aagtgctgca    9300
ttccagacaa ctcagaacct gtcacaagca gctcgactag caaacggttt cagcatggtt    9360
caccgcttaa tggcgaactt gaacgctggt atcatttgtg atgaggttga gcgtgtgttg    9420
aaaggtggta caagccgcgc tctaactgag catggtctga cacctgagtt gacacagaag    9480
ctgcgtactg cttatgctga gaacccaact ggcgtgttcc catacgagat tcaacgtgag    9540
ttggagattg tatcgacacg tgctatggac tcagtgatgc agaacattcg tactggtgag    9600
acttctcact ttgcacagtt cagtccggta ggtaagattg tggttggcta ccaatccttt    9660
gcgattgcgg ctactaacaa actactgcgc cgatacacgc agaacggtga ttacgcaggt    9720
cttgcgatgc ttatgatgta ccagttccct ctcatgctta tggctaccca tgctaagctt    9780
gcgctggatg gtaaagaggc acaaagccca cgtgaactaa tcactaacac tgcgatgaac    9840
atgtcagcta ttggtggtat cactttactg tcaccgctat ccttggtga atctccgcgc    9900 cactcattga cctcactagg ttacgtgacg cagagcattg gggcggtgca ggaaatggtc    9960
agcgatgggc gtatggacac gcaacgtatg agcaagattc ttccgttcgc gcaagagttc   10020
atgccactac gtgcagttat caacaacatg ggcgagtaat cgccctttaa agaggcttta   10080
tggcattaag tgtacaacgt gctacgagcg acggtactat gaccaacatc gtcctcagca   10140
ttgaattctt tgcacgcgt gacatttccg ttatgcttga tgagacacct gcaatcgagg   10200
gtacagacta cacttggcag ggtcgaacac aaattaactt tactaacgcc ccgttagctg   10260
atggggtaga ggttacgctt acacggcgta ccaaccgcac tgcgctgcgt catatcttct   10320
ctgagggcgc tgagttcaca cgagctaact tagacgacgc gcacacacaa ttgctgtacc   10380
taagtcaaga aatgacggag ggttctggca ttagtgactt ctatggtgac ttggatatgc   10440
accgttaccg agtgcgtaac atggcacaag gtacggagaa ccgcgacgct gtaacgttcc   10500
tccaattgaa agaggttgca gaccgtgtaa ccgcaattga gaacattaag ggtacgaacc   10560
gccgaggccc aatcactatc tccactcaat ctcccgacac cgttccggta cagtatgaag   10620
aatgggtgat gattggtgat gtggacaacg gtgcgttcgt taactcatct aacgataaag   10680
accaagagta gaggtatcta tggctgatgt actagagggt ttagccccta agcattacca   10740
cggtcagaat caggtttggt acgagaatgg caaacagtac attgcggtga acgtcggtga   10800
aaaagacgac ccggtgtatc agtaccgcga agtgctttac cgctggattg gtaacaacaa   10860
ccgctggtac ttggcctata gcaataatcc tgactctgta ggcacagtga gccttgataa   10920
cgcacgttac ttcacaggtg cgccttatcg tggtgacgta gccgtatttg tgatggtct   10980 gaaagaacta ccagacccac tcccattctt cacaggctca caatacaaac tttatagtaa   11040
tggtgctgac acacttgaga actatgttaa cttcggttat caaggcacaa agaacccgta   11100
cggtattgat aacatttacc gtatgtgtaa gctgcgtcaa gtagacgctc agtacccttta   11160 cacagttact cgccccggtc aacagggcta caactgggt gtgggtgcat cgtgggtac    11220 aatcccgact gctatctacc cgaacatttg gtcactgcaa ttccgattgg gtgacttcgt   11280
tgatggacaa gaccgcatgt ggctgctgta tggcggctct aatgtaactt ggacagaaca   11340
aggcactggt caacaaaaga gtgctcagat tagctttggt gcatgtgtat cacgttctgg   11400
tgagttgatg tactaccgtc gattcaacag tacttacgtg tacgcacgtg tgcaattagc   11460
```

```
aagtctgagt ggttggcatc aagtgcaact aacgcaggac gcgaaccaca actgcacgat    11520
tacagttgat aaaggtacgc cgaatgaaca gtcagcttcg tgctcattga agctgtgggg    11580
taaacagttt gacagtgtat tattcaactg tggccctgcg tgtgtgggta cgactggcgt    11640
ccctattgct gacgtttacg acaagtcgtg gattggcaac attgacatcc gtcgtttcta    11700
catcgacaca cacggtacgt tcaacgagaa cattgtacca cgctactacg agcaacccta    11760
ccttaacctt gagattcagg ctgagggtag caacacgtgg caggatatat cgagttctct    11820
ggtgaactgg ccgcatgagc aggataaccg ccgctgtatt tacacgctgc ctgatgtacc    11880
tgatggtcag tactttatcc ggtacaaaac caactacggt gtgagtaaca cgctaccagt    11940
gcgcatcaag ggtgacatta gccgcaagac tgagttgtat tctgacttct ctaacttgat    12000
tgaaatgcgt gagaactggc tcgttgcaca taaacaatgg ggtggtactg gcgttgtagg    12060
caaccaaact gcactgctga acggtggtgt ggtacgtgag aacgttgagg tttaccctga    12120
ctacactgat gtggcgaacg ctgtgaaagg cgtgttgcgt ttacgtggtc acggtacgta    12180
ctacgatggt gatgttattg gtgttgaccg tatcggacac cctgcccctg atggtcgtaa    12240
gactgaggta ggttcagcac tggttacacg tgagtactta gggccgggca gtttccgctg    12300
taagttgcgc tctccgtacc ggaaaggtgc ggcgacagcc ttgtggacat tccactacga    12360
ggaaatctac gagaacgacc cccgttggca gagcttcttg gacgagggct tacacgctca    12420
aggtaatgag gatgatggtt actacattgt acgtaaccac gagattgaca ttgagtatcc    12480
gactgcgttg aaagacgcac ctgatatgga ggatgtctcg gctgataaag cgcgtctgaa    12540
cacttgggag ggtgagctgc gtacttggga tttaccagag agtgacccga actacttctc    12600
tgagtacact gacttctttg agaagtgggt ggacgaggcg ttgagtgacg gtgagtggca    12660
cgagattcgt ttcgactggc acacaggcga acagaaccca ccagcaggaa aacctgcgaa    12720
acgtgtggac ttctatgttg acggtgtgtt gaaatggact aacaccacgc acatccctga    12780
cattccgggt cgtctatgga ttgccctttg gtatccacgc gcaccgggca accgttgggc    12840
tggacatagt gccgactaca tttacgactc gattgacgtt gactacttcc actacatccc    12900
gttcccagat gaaccagtgc gtcagctagg tgaaacatac cctgctgacg tatggcgaga    12960
ctggaagtgg gagaacttct tctccggttt ctataacgag ctgccgccac catatgagct    13020
acctaagccg tataatgatg acatgccaaa agatgccgat ggaacgtggt tgccaacgtc    13080
gtatctagcc gctggtaaga acccaccaca gtacatcaca ccgtaccgat tggaatggcg    13140
taatgaccgt aaattgcaag gctcaggaaa tggtgaattc cagttcttga acttagtgca    13200
aggcgctcgt tacaagatga caatcaaggt ggcacgtact acaacgcaag ccgctggttt    13260
gcagttggtg acgttcgagc cgggtgatga tgtaatcgac atcccgatgt tcgagggtga    13320
cacctacgag ttgactttca ttgcgcagag ccaacagcgg gtatctttgc gtcgtaacac    13380
aacaaacaat aaatacgagg gtctgactga catccggtta gagcgtattt aaggagtaaa    13440
catggcaaaa gctgctagtc gttcgcgtct agcggcgttg catgctgcat tcactgatgc    13500
tttgattgat gaattaaagc aatctcgtga ggaagaaatc ccacttccag ccgctgataa    13560
gtcagtgatt gctaagttcc tcaaagacaa caacatttct gccgatgcag acgatgaggc    13620
tatgggtgaa ctagccgacg agttcgagga tgaactcgcg caacgccgag aggcacgtaa    13680
acaagaactg ctaggtcgtc tccaagatgg tgacgatgat gaattagcag gtattatcta    13740
aggaggttat cgtgggttta tctgtacagg tgattacacg attaaagttg ttagcacaac    13800
```

```
gctgtaaaaa gcttgctgag aatccacgta gcatcccagt ggacacacgt caggagctgg    13860
cgttgatgtt cgcaatcaca ttcaagaact tcgaggactt cgcgtacgtt ggtatgcgat    13920
tccttgggtt cgacttaaca gacatgcaag cagacattgc tcagtacatg cagcacggcc    13980
ctcgtaagaa gatggtgtgt gcacagcgtg gtgaggcaaa gagtacactt gctgctctgt    14040
acagcgtgtg gcgtcttatc caagaccaga gcacacgtgt tcttattgta tccggtggtg    14100
agaaacaggc atccgaggtt gcaacccttg tcatccgttt gattgagaca tgggacttgc    14160
tgtgttggct acgtgccgac cctgctcgtg gcgaccgtac ctcatacgag ggttacgatg    14220
ttcactgtga cttgaaaccg ctagagaaag caccgtccgt ggcttgtgtg ggtatcaccg    14280
ctcagctaca gggtaagcgt gctgacttgc taattcccga tgatattgag acaaccaaga    14340 acgtctgac tcaaacacag cgtgagcact tgctgacaat ctcgaaagac tttgcggcaa    14400
tcaacacgca cggtgataca ctttatctgg gtacacctca gactaaagac agtatctata    14460
agacactacc ctcgcgtggt tttgaagtac gagtgtggtg tggacgtatc ccgtctatag    14520
agcaagagga aaagtacggc gacacattag ccccgtacat caagatgctg attgagcagg    14580
gcgcacgacg cactggcttc ggcgttgatg gtacgcttgg agaaactact gaccctcaac    14640
gttacgacga ggacgcgttg atagagaaag agctggactt cggcccagag ggtttcgcgt    14700
tacagtacat gctggataca accctatcag atgcgatgcg tacgcgtatc aaactgtctg    14760
atatgattat ccatgctggt gattcgaact ctgcaccgga tatgttcagt tggacagcgg    14820
ataagcgtgc cctttaccca gaggtgcatg atggtgtcct cggtgcacgc ttgtacactc    14880 cttttgagcat tgggactgag attatcccgt acaagcacaa aatcatggta atcgaccctg    14940
ctggttgtgg tggtgatgaa atctcctttg caattggtgg tgctgcgagt gcgtacgtgc    15000
acttgttcgg cacaggtggt ttccaaggtg gtgtgtctga ggaaaacatg aaccgcttga    15060
ttgacttagc tgaggacttc gaagttaagg acatcgttat cgagagcaac atgggtcatg    15120
gtacagttac aatgctgttc cagaacgccc tagcgcaacg tgacattgca cacattggtg    15180
tacgcgactt acgtaacagt acacagaaag aacgtcgtat catcgacact atctctccgg    15240
ttactcgtcg tcaccgctta gttgtccata cgtctgcatt agacatggac attgagtgct    15300
gtatgtcgta tccacgtgac cgacgctggc agtacagtgc gttcctgcaa ttacaggaca    15360
ttacgtacga caaaggctgt ctgtccaagg atgaccgcgc agatgctatc gctatgctgg    15420
ttcaagagtt gaacgcccac ttagttgagg acgaacgctc tgccgctgag aaagcactac    15480
agatgcgtgt agccgagttc attctgaacc caatggctta ccaaggcgta gacactcgcc    15540
cacgcaacaa aggcactgca agccgcctat cggtagctgg caagccactt cataaacgaa    15600
ctggtatcgg agtaggtaca ggcacattgt tccggctgaa ctcacgacac cgtaaacgag    15660
gtagactatg aacaaacgat tagactcatt taaacgtgaa gactggttcg tcttctacg    15720 tacaattgct gactttatcc tacgtcgcaa aaacaagtaa tgtaaggagc tgctaatggc    15780
agagaaagat gctgtcttca tgcaggactt tgaggacaaa tctacacgag aaatcctttt    15840
agaccacgaa cgacggttat tcgctatgga acagacacag aaagaacttg cagacagttt    15900
gaagcaaatg cgtgaagact ccgcagaaat gttgaaaacc tttaaggaag ttgcacctgt    15960
ggttaagaag actttgtact tcttagcagg tgttggtgct gtgtacttag tgggtggaga    16020
tggtaagctt ttagagactg ccgttaacgt cgcaactaaa ttagctgcaa tgtaggagac    16080
tgtatgcaaa ttgtaatccc ctatcgcaag ccgggattac cagttattcc gtgggtacgc    16140
gctgctgtgc gtatccgcgc tagtgagtta ctgcgttggg aatttcctga cgagttaccg    16200
```

```
ccagatgtat tagcccagtt cgtacaggac tgtcgtgaag cttacccagt gttacgcgag    16260
ggtcaagtgg aggcgatact aggaatggac actgtagctc cggtagagta cacgcatagc    16320
attgaagccg ctgtactggt ggctgacgct gtggttggtt tcaaccccgg taatgggtca    16380
ctaactccgg tgtacgtctc tgacggtact acagatgccc gagtgtacgc tctggaggtg    16440
aataacgcgt ctagcttctg ccgcttaacg ttggcagata acctagacct gttcaccaca    16500
ttcactatgg gttatggtaa cacgtacacc actttgacca aggctggtaa gaaccgatgg    16560
gagacaccta agacgatga tggtgttgcg tttacagacg ctatgtacaa tctattgaac    16620
gataacatag gtgtacctgt ggcatttgat ttaattggta ataagtagag gtaagtatgt    16680
tacttagaga cactgcgaat ttcaagattg tgaagttcgc gtgtcaacac tgtggggctt    16740
tgaaactaga cttagcctta cttatgttgg cacaagcact acgggagcac ttcggagaac    16800
cgctaaaggt tgaatccggt tatcgctgcc ctgtacacaa caaagctgta ggcggtgctg    16860
agaactctcg tcacttacat ggtgatgcag tggacttgca cttgctgaac aaagaccggg    16920
ggaacttcca gaagctccag aagctgtacg acacggcttt agctctgaac cctaacggtg    16980
gtgtaggtct gtacgactgg ggcgtacaca ttgatacacg tggtgagaaa gcccgatggg    17040
attaccgctc tgataaatac aaagaagtaa tggggaaaat ggatgtctga acataaggta    17100
acacaggaac tcgtagagtc aaaggttaag tctgagcagt acgtggttgt accgggtact    17160
actctgacgt tctgtgtgtt aacactagag aatggcttca ctgtcacagg tgagtcagct    17220
tgtgttgacc cagagaactt cgacaaagcg gttggagagc attgggctaa ggtggatgcc    17280
atgaagaaag tgtggcctct tgaagcgtac ctgatgaagc agaagctgca tgaagctgag    17340
ctagagaaag agcgtacgtt cttagcaatg gcagttcgtg gtgaagcgca gcgaagtgaa    17400
acgaagcaag ctgaacacaa gcggtgtac gagggttaag ccctttgaca cgaagtgtcc    17460
atgtgtagag agtggaaagc taatggaaag ccagtggtaa catagggaaa gcctgtgaaa    17520
gccattggcc tcctagcgga aagcgtgtaa aaccctgcac aagaaaaatg ttatactcag    17580 ccgaggggt tctcccccat ccacgcccgc gtttccccg tggggtgcg tgtgtgtgcg    17640 ctggcgtgcg tgcgctcgcg tgtgtgtgca tgggtgtacg tgtgcgtgcg tgtgcatgcg    17700
cgagctatcc agcgcgtgcg cgtgtgtgcg tgtgctgcgc gtgtgctatc cgtgggaaag    17760
cgatgggaaa gcctggcgat tgttggcggc tacgtgagcg gcgctgctgt gctctatgct    17820 tgccttttt gctcgcctgt tctctcactg gcttgtcact tgtcagcgtg tggctatcta    17880
ctggctatcc acttgctacc atacggcgtc tatgacgcgc tatgctatcc gcttgctatc    17940
cagtgttagc acttgctatc gtgctgctat ccagttgcta tcctattgat ttacgctttg    18000
tcgctctcgc ttcgcttcgc tccgtcgcta caatagggaa tgtttgctag tgttagtcag    18060
tggacatacg gcgacagggg acactccgct tcgctccgtg tcggtcgcct cctgtcaggg    18120
gactaagaac attataccgg attgaacatt gagagactag gcgattaggt gtggataact    18180
cattgttagg atactgtata accactgtat aaaccgcttt tattgtgata cacctcacat    18240
ttctagtcgc agggcttgat tatccagtct aggtatggga tagttcattc cgtcgagagg    18300
cactagccac ttagacaacg ctctttaata atctggttca tgccgtcagg ctaggggatg    18360
ccacgtataa cgtaggggta tcgcttgtag tcgggtagtt gtacagtcaa acattggata    18420
atacgttgtt atccgttgga ttatcaagag gcttgcagcg tgaactggat tagagcttgc    18480
tctttaaaat atgcttgaca atgaaacact aggtagtgta acttaaatag cgtactcagt    18540
```

```
gagtcacaac taagtgcctt tgatgctaag gttaaacaat gcaaagcggc gtttgctggc      18600
ttagttgtaa agtgttggaa ttaccgctta cagcgtgacc gactgactca acactgaatc      18660
aaaaaacgct tgacaggttg aacaacttag tgatacatta gaaagcatgt tagggcaacc      18720
taacgactca aggcattacg ccagtcctgc gggacactat gaaaccttgc gaggtactgc      18780
atagcaaacg gcactagcca gcgagtcatc gcctactaag gcatcgttct ttaaaaattc      18840
ggtaaacggt ctaacactca agcgagagca gttattgcca ccatctgcaa gcgacacgga      18900
tacacttgtg tctgctgtaa ggggtcagcg agaagcgaag cgagtagagt taaaagtaag      18960
agttagacga cgggtaatgt ggctgataac cactgcatcc ggtgaattgt aagtgtaaag      19020
tagtcaggct tgaaatccgt atacagtttt ccgcttacga tgtactggca tcaactgagc      19080
cagcggcagt ctatcccgaa agcatagacc attcgatagg gcttagtgta atcattaact      19140
gtctgctaac acgatatgtt ctctgagtcc tatccaatgt aatcttgtgc aacctagcac      19200
gaagcggtgt gacagtccta tcaagcgcaa tcttttaacc attggtcaaa gtctatgggg      19260
tatttgtgtg cgatgtgctg gtagggtagc ttgtttcacc gcttatttta tcgaggtgaa      19320
ctatgttcaa acgtttaaag caactgtcaa aaagttttta cttgactttc attagaccgc      19380
gccgtgtgta ccactttgaa gtggtctatc gtgacagtat gcgccgtgtt caaaagaaac      19440
actttcaagt gtgcgcaagg actcgcaatg aagcttatgg tctagcgcgt cacgttagct      19500
atatcaacaa tgtgcgaggc tacaagctat cgctcactaa tgtatcactg tttgacggtg      19560
gtcaatcaat gcaatctgca tactaatctt taatcgccaa acgagggcta aactatgtca      19620
actgtaacaa caaacaaagc accaaaacta acgtctgtaa aacaaatccg tactcaactt      19680
gtcaaagctg agactatgcg ccgtaatgta actatcagtg cgctgtacca tgccttagtg      19740
aagtctaacg tcgcatggat ggataactgg acacgtactg acgccgctat gcttgacgca      19800
actctgcgtg ttctatgccc gactaagtgg gttaaaccgg atgcaagcaa gggtatcaaa      19860
ggtcattaca agcgcgacac caagaaagct gatgaaatca tgggcaaact aggtgtaaac      19920
cgtgaaatga cataccaga gttttaccca atccttgagc agtactggct tgagaactca      19980
gagaagaaaa agtctgagga actgacactc gaccaaaaac aaggcaagtt gaaaggtcaa      20040
atggcgcgtc tgttggggca gtgggctgag gctggtctgt catacggcga agttgaaact      20100
atgctcaagc gtgcacgtga cggtaaagac attctaccaa aggcgaagta atcatggcac      20160
tgaatgcgag agagctacag ttcctacgtg agaactacgg gactgttggg aagtgtctat      20220
caaaacaggg cgtcgctgat gcccttggta agacgtacaa tgagataagt cacgctatcc      20280
ggtacaatgg tattacaact ggcgacaagc gacgttcagg gcgtaaacta actgagtctc      20340
aaaagcgtga gcttgtgcaa cagaaagacc gaggacgtag cagtgagttc ttagctggct      20400
actacgggat aactccgcag catgtgtgcc gtgtgtaccg tgctgctaag caacagaaat      20460
attaggggat tagtatgtct aaactaaaac agtggtgggc gaagcacgct gaacgcttcc      20520
tgtttatggc tgtgtttgcc gtgatgattg tgtgtatttt cattatcggt tgggggttca      20580
aggcacttga gctgatgttt tacaagtggg cgttggggtt ttaacatggc aactttgacc      20640
aaggggtata tgaatgctca agagcatgct gagtacctaa aaactgagca cttgaaactg      20700
caagatgctt tccacaagta ccataatcac acacgtaaac gtcaagaaac gctgcgcgat      20760
atttactcag aacgtgctcg tgtagtgggc ttgtctcttg ccacttactg caagcgtttc      20820
aatatccgtg gtgttttgtt caaaggagaa ctggatgcga atctatcaaa tggtagcgcg      20880
taacttcaac agtggtcaca tccaccgcat catccgaaag aatcttgagc aaggtgagaa      20940
```

```
gttaaccctg cgtgattcaa ccgcacttat ttggttcatg ctaagtgagc aaaagtcttt    21000
ccggttgtca taccaagaac tgcaactggt acaccctaaa ctgcgcaagc tgctaccact    21060
tgagcgcaag ctgtgccacc gtacactgac tgatggtact caggtactag acacggtacg    21120
attctactct gagacgtatg ctagacgtac tctcaagcta ctcaaagagc acggtcaata    21180
tgatttactg actgagctaa ccaacggtca agagcaagca ttcaatgcaa tgttcgaggc    21240
tacccaacgt atagcaaacg catggcaatc tgacatgctt gactgattaa atacaaatca    21300
aacactactc atgtaaggag ttccaaatgt ctaagttttt ccaaccattc gaagcaatcc    21360
aattgttcgg cgttaacgac cctgatggtt acaagctact cgctgagcat tctgagaatg    21420
tcgttgagcg attcactgta atgccagctt tctacagccg tgtagcctca gagaacgtgg    21480
atttcatggg gcaaagtggt aaggtgttcc cgtacctacc acgctacggt aagaacgccc    21540
ctcaaggtga gtcaactgat gtaacctcgg ctatcggtaa agagactgtt agctcacgcc    21600
acttcatcat gaaccaacgc agctgtgatg accgcaaact tgaagccttg ttcatcggtt    21660
tatgtcctga ctggtacagc acacaagtac tcactgcaca ccaccaacgc ggtatgttcg    21720
actctttcgc tggttggatg aacttcggct ggaaccgtgg tggtaaggct atctctccac    21780
gtactacgct gctgcgtgag aagttcgaag cgtacgaggg tactcaacgt ggctgggtat    21840
tcaaagcgtg ccaacgtatt gcacgagtac actacgcaac taactactta caaatgtctg    21900
acagcggtta tcagagtatt caaccggatg ttaatggtac tgactctccc gaccgcatct    21960
ttgttagggc aggtgatgat gaaatctctg cgcttatccg tgctaaacac actggcttgc    22020
aagggttgga ttttgactct gaaatgtcgt acgaaatgca ggtacaccaa ctgagtgagt    22080
acgtgctgaa cgctgctaaa ttactaggtt acaaccaccc taagctactg ctttcattg    22140 aagaatactg tgcaaacgtt atcttcttag gtactgatag catctgcaaa ggcattcgcc    22200
tagcgaacgt actgcatgag tgctggtaca aagactatga cctacacttc ggtgcgccta    22260
gtttcagtgg tcttgacggt ctaatcgttc gttttctacg tgcttggaac tgcttcttcc    22320
agaaccaagg tgtaacacct gtcggtctaa tctgggacgg tgaaagcgaa gtgaagcaca    22380
tcactgctaa gcctactgcc gttgtaacta acgatggtcg tgtgcaagtt cgccttatca    22440
tcaatgactt accaatccca cgcttatacg ctgatggttc tgattaccgt gacgcactgc    22500
aagcgatgaa agcactgaac tctccaatcc atacaacaat catcccggct gagcctgagt    22560
atgaccatat ctggcacttc gtgtacgaga cgggcccaag ctcatgtatg actgactacc    22620
cgtatgaccg ttgtccggtg cgtgtgtact gtcacgaaga caacagcctt ggtctagctg    22680
tgtgctaccg ctcgccacgt gagttaactg ttgacgagtt caatgtgctg gcaagccaag    22740
gtgagctgga tacaccggag ttctctgcta aggatgtgtt cattagcatc actggtcgtg    22800
ctgtgtgtaa cattgacgac aagcagtacg ttcgctcata cggttgtaac actgaggggc    22860
acttgatgaa cgctggttac aatcacaact caagctgtct tgatggtcaa gagctacgtt    22920
acatcgagta cactagcggt gctgatactg tgcttatgcc ttaccttgac ggctacgaag    22980 aaacgttga gctgtgtgag ggtgcgaaag gcaagtactt cttggtgtgt gatggtggtt    23040
ctgacactta cgaggcacaa agcgcatctg gatacattga aatcaacctt gaagaatgct    23100
atgagtgtga tactggcact cacgaggatg atatgtgcac tgtgtatgag ggggacatg    23160 aacgccgtgt gtgtgagagt tgccgtgacc gctattacgt gtgggttgac catgataacg    23220
actaccacca tcaaagcgat gtgacttttc ctgagtacac tggtgagtac atccttgacg    23280
```

```
acgagttgga agtgtgtcca ctggtcggcc cgatgcacga agaccgcatg gatgagtgtg    23340
aagcaactgg caagcgtgtg ttcgaagacc gtcttgttga tgggtgcttg acatccgaag    23400
acgcagcaac gcttggtgtc cttgacgagt ggttagacta ccaccgcgaa gacgaagacg    23460
aagaataata actactacaa ttaaggagtc gtgatgacta acccaaacaa ctcaaaagct    23520
ttcgaactac taacagcaat cctaagcgaa gaacgtcccg gtttacgtgg gcaggaagtg    23580
gtagccgaag tgcttgacgc tgagggtatt gagtactcga cggacagaca tgggaacatg    23640
tttgtacaag tgggtgagcg tgatgacatc atgttcacaa gccacacaga tacggttgac    23700
tttgatgcaa catcctaccc taagtggtta caagatgggt tcaaggaaga cgctggtgag    23760
ttatctaagc tacctaaaga gaaaaagcta tgtgtcttga acgggcactt agcactggat    23820
gccgatggta tctgggactg tctcggtgct gatgatggtg ctggtgtcgt gcttatgatt    23880
atgatgatta agcaaggcat tcaagggcag tactggttct ttgctgagga agaagtaggg    23940
cgcgttggtt caaccggagc gtacgaagat gatactgagt cattcgagaa agtgaagtgg    24000
tgtatcagct ttgaccgccg tggtactgac atcatccata ctcagattgg tgggcgctgt    24060
gcctcggatg aatttgtgga agcactggct gaacgctttg accgtccaaa gtcacgtatc    24120
acaacaggtg tttacactga ctcggcaacg ttcatcgaca caatccctga gtgtacgaac    24180
atcggtgttg gttactacaa tgagcacact gaccgcgaga cgctgaactt gaacgagttc    24240
tacgatacgc ttgagcactg cttgaagcct gagacttggg ctgagctgcc agtgggtgaa    24300
cgtccagaac ctgcacctgt accttgggtc gatgaggact tcgaccttga cgattacttg    24360
aatcgccttg acaacgccac tgatattgac gaagtgttgc ttgagtttgg tgctaagggt    24420
gagttagaaa tgcttgagtg ggtgcagaca catccactac tggcggctag tatcctgtac    24480
cttgcaggta atcagacagc acgtggttgt atcggtaaag acattcgccg cgctgtggat    24540
gacgaggggc gtacccttga tgacctagtg cgtatgatgc gcaaaactat tcagtaactt    24600
aaattgcact taggaggtgc ttatgtattg gttaatcatt gctttgacat ggggtggcag    24660
tgctccggtt gctgtgccta ttcaagacga ggcgacttgt atctcagaga gtaagcgcct    24720
tgaccgtact gcgtatgttc agtacacact gtgtgttaag tctagtgacg aaaaggtaag    24780
acagtaatgg acgcgccgtg gttaagagct tgtaagcgtt tagccattgg tcagactaga    24840
cgctttcgct gctgtggtgc taccgcagcg gctatcttgt acaacaatcc gcagtcgtgg    24900
gaaatgtggt gtaaccgctg taagcagacc accaaggagt ataagaagta tgtacgcctt    24960
gatgccaccg tgcatgagcg gagcatgcag cctgtaccta cagatgcttt atgtattagc    25020
cagacgagtg cggaaataca gcactttgtg ttttcatatc ttacaagcaa aggtatatca    25080
ccgaacatgt tggaggacgt atgtcgctta gagtggtcag agagcaaagg gcggataatc    25140
ttccgcttcg agaacgtggt tcttgggcgg agcatatcac cgaacgtaac gccgaagtgg    25200
gttcaatatg ggagcaactt ccagacatta gtgaacttga aacccgattg tatgcagccc    25260
tcgctagtgg tgcttaccga ggatacattg agtgcgataa aggtgcagta cgtggcgaac    25320
ttgttcttca agggacgcgt actggtcgta tcgacactcg gcactacaat ctctctaacc    25380
gtccgggcac ttttagcgtc ccttatggag cagacgggca gtaagccaaa cgtcctctgt    25440
tggtacgacg gagataaggc aggaattgac ggagcacgga aagctcagaa agtactacga    25500
ccattcgcaa atgtacatcc cctaacaatc gacggcaaag acccgaaaga ttgtgaaccg    25560
acacagatta aagaggtttt atggacgcag ttatcgtaaa ggcattgtgt gacaagacac    25620
gctacagcaa cttattgcct tacgttccta aagacatgct agcaccggat acttccgcgc    25680
```

```
tgcttagttg ggttgggctt tactggaaga cctatcctga gcacgacgaa gtagactttg   25740
cggcattcaa tagcatggtt tcgttacgag ccacgcagag cacacccgaa gaactggcaa   25800
ccatgaaagc actaactcat gaagtgcaag cggttgacga ttccagtgtc gatggggttg   25860
taactatgat gcacgagctg gcgtattctg gacgagcggc aagcatcctc acgaagtacc   25920
aagcaggtga agaaatcgac ctgatgtatg aaatgaagaa gcttcaacgg gagttcggtg   25980
ataatgtcaa gactcagaat gagttgttct catgggaaga ccgtgggctt gacgacgtac   26040
tagcagcgaa cgaggagggc gcaggtctga aactacgccg cttcggtcag ctccgtcata   26100
atatccgtgc tctgcgtggt ggcgatacag tggcagttgc cgcacctgtt gacgcaggta   26160
agacatcact acttgctgca atcgctgctg actttgctaa ccaaatgaag tgtgcccctg   26220
agcgttatgg tgacagacct atcctatggc tagtgaacga atcaatggct gtgcgaactg   26280
tgccacgtat ttaccaagcc gcaactggta agacattggc agagattcgt gagctgcacc   26340
gtgagggaca gttcgagccg ttgtacttag ctgaggtggg tgactggcat cgtatccgtg   26400
tcaaggacgc acactcaatc accatgccac agattgcaac gctggtggaa gaaatgaacc   26460
ctgctgtggt aatcatcgac atggtggcaa acatccgtgg tggcactgct gagacagagc   26520
accagaacct agaagcgaag tggcaggagc tgcgttcgct ggcttgtgag cacgacttcc   26580
tgatggttgg tacaatgcag ttcagtgccg aggggttatga tatgttgtac ccaccgctga   26640
cagccttgaa gcaatctaag attggtgtgc aaggtgcact ggatgtggca ctgttcatgg   26700
gtaaacttaa caacgatact gagggcttgc gagggcttag cacacctaag aacaagtgtc   26760
cggtatccgg tagaccgagc gtgaaccagt tcgaagtcct gttcgacgct caacgatgtc   26820
aattcaattg tggcttcgca gaatcggcta tggaggctta atggaaaagg tgaaacgtgt   26880
gtttcatcca gcgtcggggg ctaatcgcag tccccatgct gtccgaatca aggtaaatg    26940 tgttcgtact ggtgacgagc attactatca tagcatcgga caggcggtgg atgatggttg   27000
gtgtcgcaaa ggtattagaa gatgcctacg tggtgagcaa atacagtcga acggaatgtt   27060
ctgggcgact tggatggag tagagcatga gtagtgtatt atttatagat ttggagactg    27120
agaaccatga gtaccacggt agtaaagcca gtccgtactg tccagacaac tatatcgtgg   27180
agtcaggatt tagagttgac cgcaagaaac ctgatggaac tacagaggtc ggtggtattg   27240
agagtgtgcg atacgattca cgagaagctt tcgttaacgc tccaacaact gagtggctac   27300
ccattcccga agactgttgg ctcatcgttg ctcataatgc cgcttatgaa gtttcatggt   27360
tcttgcagtt cgcgagagaa gcatttgagt cttttcttgcg tcgtggggt cgagtgttct    27420 gtaccatgca cggagaatac cttgccactg accaaacttc cctgtatccg agtctcgatg   27480
aaacagctcc caaatacgga ggaactcata agtggatgg tatcaagctt ttgtgggagc    27540
agggtgttct cacgagtgag attgaccccca tcctgttaca tgagtatctc gcagggccga   27600
atggagacgt tgccaatacc gccttatgtt tctacggtca atgcgccgtt cttgcagaac   27660
aaggaaagtt cccgttggtt tgggagcgta tggacgcctt gctgagcttt gcgttctgtg   27720
agtggttcgg tctgtacgtg aacatgccag tggctcagaa gaaccaagcg gttcaagaag   27780
ctgagattgc agagttaacc actcgcctca gaacgtacct accggatgac ctaccggaag   27840
aaatcgactt caactggggt tctgacttcc acatgtcggc gttgctttac ggtggcccga   27900
ttaagtacaa gaagaaagtg cactatgaca agccaaccta cgtcaaggtt gatgcgtacc   27960
aactgcatga gcatgtgagc gatgaccgtc taggcggtga accttggtat gacccaatcg   28020
```

```
acggcgcgaa gtacatcaca cctgagactt acgagaagta cagactatgc cctgctgatg    28080
ttgtggtgta taagtccggt aaaaacaagg gcttacgtaa ggtgttccgt gctaatacga    28140
acgaactcaa gatgaagtgg ggcgaagctg tgtaccagtg tccgggcttg tgtaaaatct    28200
cagagctgcc tgagcacttc caagacaagt tcggtgagcg tggtgagttc cgccagaacc    28260
gcacactatg tgatggttcg ccagtgttta gctcaagtgg tgactgtatg gctggtctag    28320
ctaagcaggg ctttgagttc gctagtgaca tttcccgact ggcaacgctt gagaaagaca    28380
caggtactta ctatctgcgc catgaatacg atgacgaggg taacatcact aaatcaagtg    28440
ggatgttaca gtacgttatc cctgagaagc ctgatggttc gggtatcatc caccacagac    28500
ttaacacttg tgcaacagtg acaggtcgct tgtctgcgtc gaacccgaac ttgcagaacc    28560
tgccgcgtgc tgaggaagac aaggacggca acgcgaagtc ccgtgttaaa gaaatgttta    28620
cctcacgctt tggcgaagat ggtcgcatca ttgaggtgga ctactctgcg ctggaagttg    28680
taatgggcgt tgtacacact ggcgatatga agctgcttga gctgcttaaa gctggtactg    28740
atatgcactg ttaccgcctc gcgttccaag agaacttaga ctatgaagaa gtgtaccgtc    28800
gctgtcatga cgagggcttc gagttccatg ctctgtggaa gtcgatgcgt actgcaatca    28860
aagcacctag ttttgcggct cagtacggcg cgtcagccgc tggtatcgca ttcgctactg    28920
gttgtactgt cgagttcgct caagcgttcc tagacaacga ggcggcgcta ttccctgata    28980
cagctaagtt ccgtcaggta atccgtgacg aggttgagcg tactggtaac ttaccgggta    29040
acttgaaacg tgaaatgacc gacgacggtt ctgttcgact gtaccgccgt ggttactgga    29100
cgtcccctgc tggtatgcgt tacagcttcc gtcaggttga gcgttgggtt aagcgtgccg    29160
atggtcgtgg catggaaaaa gtcatggact acaaggatac acagcttgct aactactggt    29220
gtcaaggcga ggcgttcttc ctcatggcgg ttgcattcgg tatgattctg cgccacatga    29280
ttgctaagaa ctggtacgac aaccaagtat gtctaatcac gaacgttcac gatgctgcgt    29340
acctagacgc tgctaacgag gaagtgggac gtgaggctgc actagctgtg aaagacatca    29400
tggagcgtgc taaagaccgc atcctgcaac tatggcctaa ctacggtcac ttgaaagacg    29460
taccattccc tgctgctgcg gaaatggggtt catcaatgta caacaaaaca cacattcact    29520
aagagagatt ctactatggc tactatccga ttaaacgctg acaaacgtcg tacaattctg    29580
aacaacatca tgactgagtg gaaagcgaaa caccctgccc caaccgctcc taaattgaat    29640
gcacgagccg ctttcgttaa agcctatcaa gagttatggt acaaacgctc aggcattgag    29700
aaagcggttc agaacggcct cacaccaacg gcactgcaca ctagctcatc actgcacctg    29760
tacatccaag accgcactgg taaagctcta ggtacggttt gggaatactt ccgtgatggt    29820
gagaatggta ctatcaaact gcgtgtaccg aatggcacaa cggtagttta caacgatgac    29880
ccactgtacc tacagtactt gaaagataaa agtgctgatg acaagtacga gattgatgtt    29940
gagcagtggc acgaagaaca ccgcacacaa gcacgtgtgt acaaacaagc acttgagcag    30000
ttcaagacgc ttaaacagtt gaccgatggt tgggacggca ttgagaagta cctaccggaa    30060
gaattcgaag tgcagtcaac cgctgtggct gttatccctc aactaccata ggagttcaca    30120
tggataagca tatactagac attgcagctc atgacatcat gcagcttgta cgggctacag    30180
tgaaagactc ttatgaggtg gctgtcgctg gtggtgctgt gcgagacatg gcgcgaggct    30240
ttaagccgaa agacctagac attgtggtag cgtgtggcga ctcatgtacc gctcaagtat    30300
ttgattggat gtctaagatg agcagccaac tgagtcaggt gaatatcgct agtgaggtgt    30360
tcttagccta caccgatgac cctgataact gtgacagtga cttttgacgag aagctgtacg    30420
```

```
gcggtatcaa gattaagcat ccggtcattg agattgatgt cctgttcagc cgcaaaccta    30480
gcatgaacga agcggtagct gactttgatt gtgaattgaa tcgtgtctgg acagacgata    30540
tgcgcttcat taagggggcgt ctatacacaa ttgatacatt cgcacaaggt tatcctttag    30600
```

(The line at 30600 reads: tgcgcttcat taaggggcgt ctatacacaa ttgatacatt cgcacaaggt tatcctttag)

```
tgcgcttcat taaggggcgt ctatacacaa ttgatacatt cgcacaaggt tatcctttag    30600
tgcttggtac agcgcgtact gggcgtgctg ataagatgat tgagttgtgt gcgaagtatg    30660
attgcatccc tgttatgcac gacctgtcta aattagacga gttacgagag taatagggtg    30720
tggaacctcg cggcgggtga accgagccta gcatggattt gttcatccgt caaataataa    30780
ttaaaaagtt acagggctaa gtcagccttt caaaagaaac ccttgacaaa ccattctccc    30840
tgtgagtctc ccctctttaa agagtcacgt acagggagaa agacaacaaa cctaacagta    30900
ctgaggtaat attaatgact actccattta acccactaga ccaattgaac tcacttgtag    30960
acgctgctgt tgaaactcaa gcagttgata tgaccgagac tggcactggt ggtggtgaga    31020
aaatcatcct gccgaaaggc ccatacaact gccgcatgat tgagtacatc gagtacggta    31080
aagttgtacc gacgcaccaa ggtaaaccaa ctggtcgccc tgctgcgctg aatgctcgtg    31140
ttggtttctg tttctacggc ccgaatggtg aagaagttta cattcgctcg ttgaagatgc    31200
cagttagcaa ccacgagaaa gcaaacgcta agaagctgtt tgaccgcatg aactacactg    31260
gtacgttgaa gcaccttgct caaggtctga accaatgttt ccgtatggaa attgatgtgc    31320
aagagaaaga cggtcgtgag tacaacacga tgaagttcga aactctgtca ccgcttccta    31380
agttcgaccc agaaacaggt gagcctatca cactacctga gttcgacact tcgaaaatcc    31440
aagtgttcct atgggctaac ccaactaaag aaacttggga ctcgctgtac attgatggta    31500
ctgatgacaa aggcaagtct aagaacttca ttcaagaaga catcttgaaa gctgtggact    31560
acgagggttc accacttcaa gctctacttg agggtggtct accaatgcca ccagccgaag    31620
aacctaaagc tgaatcagca ccaacacagg cagaccacgc agcagcagca gcagccgcaa    31680
tgcctgatgc acctgcaatg ccaacaatgc cagacgcacc agcagtctaa ccatgaaccg    31740
ggcggtgcaa gccgccccctt aactgaggat acagaatgga catcactcaa ttcgcacaac    31800
```

(Line at 31800 reads: ggcggtgcaa gccgcccctt aactgaggat acagaatgga catcactcaa ttcgcacaac)

```
gcattaagaa agcgtattcg ttccagaccg acatcgagcg tatcgtcacg gactacaaag    31860
agcagaccgt taaggtgtac cgccgtggta aagtgctacc tcgtgtgtac cgcttgagca    31920
tcatcaacaa gtccggcggt cttaaacaga ataccgctc atgggctatg acgaactaca    31980
tgctagtaat cggcggtgac gctggtgctc acatggcaca gtactctggt atcatgaacg    32040
acgacaacgt ggttatgctt gaagacttca agacactgac caaccatcaa atcatcaacc    32100
cacgataagg aactgaaaaa tggatgagaa acaagcacag aacgtagccg agcaggaagt    32160
tcaagtagta gcgtacaact gtggcgaggg cttacgtgag ctgttcggca aaatccgtga    32220
gtgggctggc gctcgaaaca ttctgaaagg ttgtacccca ctggctcagg cttgtaagct    32280
gtcagaagaa atgagcgaag tgattaccgc tatcgtgaaa ggcaaactag atttgcttaa    32340
agacggtatc ggcgactccg ttgtagtact tgacatcatt gcggcacagc ttggtgctga    32400
cttcgaagac gtagtgaaca cctctgacta cactcagatg ctggcacagc ttgaagcagt    32460
agcagcactt caccctgaga gaaccgtgc tggtattatc ggtacgctga atgctcagac    32520
```

(32520 reads: ...agaaccgtgc tggtattatc ggtacgctga atgctcagac)

```
gtcggacatt atcggtgcgt tgtataacta cgacgtcgca aatgaggaat cattggcaga    32580
cgctgtgatt gctattgagc acctacgccg catgtactgt acactgtaca tcattgcaca    32640
tcactacgac cttacgttgt acgagtgtgt gaactttgcc tacggtgaaa tcaaagaccg    32700
caaaggtgaa atgcgcgacg gcgtgttcgt taaggaagct gacttgtaat gttaacgtac    32760
```

```
ttccctgatg ctacgctgct ttgcatagac gatactgatg gggaactgtg ggttatcaat      32820
ggtggctgga atctcaagtt agacggagag gaagccaccg tcgtcatgac aggtaagcgt      32880
attaaagtag gtaaggcaga gcgtcttacc cgtgatgagt ttgaaaagaa ataccctaac      32940
tttgggtact aaggaaaagt aatgtttaaa tggttaaaga agaagttcaa tgaattggtc      33000
aataaataca aagatactaa cgtgggggtg gcttttaagc ggtttctggc agtaccatta      33060
cttgccgtgt ttgggtatga tatttatgtt atggctaata gtcctagctt tgctcacttc      33120
atgggaatta gtatcgactt ggtgcttatg atgtggtggg ttgagtggct gcttggtggt      33180
gataagaccg tcctagacct cgacgtgttc aataaacatt gggtcggacg tttactgtta      33240
gtgctcttgt tcttagtagc attacctgca atcctaatct tagccgtggt aacgtggttt      33300
atcttggaat ttatccccga agtctcacgc gactttaagt taacagtacg tgaaatgtgg      33360
gatttcatta agactgggaa tcactaatta tgacaggcat tcatggatta aacttggatg      33420
ccttggacga ccagttcgct atcgttgact caggtcaagt cctcatcctt gatgggggact      33480 tttacttgta tcaagcagcc gcaaccgtta agacattgcc gactgcgatt cgacgcttcc      33540
actctctgat tctacaggaa atgttctact cgaactgtaa aaccgctgag gtgtattgca      33600
cagacagtaa ctcacctaag tgtctacgtc cattgtatcc aacattcaaa ccatatcagg      33660
caaaccgtaa aggtaagcag aagccaccgc tgcttgatat gttgaagcaa gctgtgcaga      33720
acatggaact gcacgagcat cccgacggta tctcggtagt gtgggcgttc gaggaagaag      33780
ccgacgacct gatgatacag cgtggtgagg aactgtaccc gaacgggctt atcagttccg      33840
gtgacaaaga tttgcgcatg actcgtgccc cgtactggga gcagaaactc gctatcacta      33900
gcacaatcga caatcgcttc ggttatgtga agtggtacga gggtgagaac atgccactca      33960
aaggtcacgg cacggcattc ttctgggcgc aaatgctcat gggagactca gccgataaca      34020
tccgtggcat tgaccgctta gacggtaagt tgtgtgggcc aactaaagcc tacgaattct      34080
taacagacct tatcactggt tcgccagatg atgagacaac agtagctaat accatcattg      34140
gtaagtacgc tgctgctcgc caagacccac tagctgaggc agaaatgctc tggttacgtc      34200
ggtctgctga tgattctgga tacgcctacc ttatggaagt cgtaactgtc cctgagtatc      34260
gcaactggct ggagcagttg catacgtatc acatggcggt tatcaaacat aaacaggata      34320
atccagatga agaagcctag taaaaaccat gcagtgaagt tgtatgagcg tgccttggag      34380
ttgtggtaca aggacagcaa acctgagaca cgtgctcaat tagaagccac catgattgaa      34440
ctgcgtgata ctgaccgcga catgtggcag tcagcgttca accagattaa ggaagatatg      34500
gacatggagg cactagctaa tgagttcgtc taagacttta cgaaaggtta ctcgcgccca      34560
gttacgaact attgggcgca aacttggggc tgagcaaggg ggcaagtgtc ccctgtgctt      34620
gaatgactta cagttcagta ctaaaggtgc tgtagttgta gaccacaacc acgagacagg      34680
agagattcgt ggtgcacttt gccgttcctg taacgcagga gagggcaagg ttgcaaacgc      34740
tgtagggcgt tggattgttg gtaaaatgga ttaccagcaa atcatccctg ctctgcgtcg      34800
cctagcagac tacctcgaaa gcacggagaa agagggaact ggcttaatgt atcccggtca      34860
taagactgag gaagacaagc gtgctgctcg tgcgaagaaa gaacgtgccc gtcgtgcagc      34920
cgctcgtaaa atgcgtgcgc gttctaagga gcaagaataa tggtgagtgg tgagaaaccc      34980
tcagaatggt gtgcccgcat gagtcgtgaa gctaaggacg gtgacacggc ttatcactat      35040
tggcaaatgc aacgacattg ggagaataaa ggtctatgat taaatgttta attctgaatg      35100
gcccaccggg tattggtaag gatacgttag ctgaaatgtt acgtgaccat tacctgatga      35160
```

```
atgcctttaa cctagcagtg aaagatgcac tgtaccgtga tgctgcgaag catgtgggta    35220
tggcgttgcc taagttcatc gcactggcgt ctgaccgtaa cacgaaagac gtaggtcaaa    35280
ttgagttagg tggtaagtca ccacgtgaag tgcttattca tgtgagtgag gacatcatca    35340
agcctcagtt cggtgctgac cactacggta aaatggctgg tgctcgtgct gctgaggtgt    35400
tagaatacgg gcgtattccg gtattcaccg actgtggctt cccagaggaa gcggttagcg    35460
tcgctgactt cattgaacac agccctatgg tggtgaggt gttggttgtc cgtatgtatg    35520
gtcgtggctg tacgttcgct aacgatagcc gcagttactt aactgtgaaa catcctgcga    35580 ttgaataccct cgacgtagtg atgattgagg gtaaaccgga ggccgcatgt cgaaccatcg    35640
tggagcgtct gcggagttag tctttgtgga tgaagcacct gtgaatgtgg ataaagagta    35700
cgcaatcata gcaggtatga tacaatccgg tatgagcggt gcagcaaggt cgctgtactt    35760
taaggttacg gatgctgaga acgccgtgt gctgcgtctt atgattcagc gcaatttgaa    35820
aacaacgttg taatttggag tgtttatgtc tgtcaccaag aatcgtgaga catttgaaga    35880
aaaagccgct cgtcaagagc gcattgaaga aacgtttaag actgaggcga ttgaacgcag    35940
ccgcaaagct gtactagatg ccttggagaa tggtcgtgct actgagttaa cacctgtgca    36000
acgtctgctg aatgcagcgt atgatggtgt gagcgcccga attgacgagc tgaaagcttc    36060
taagactcgt ggcgttggtg ctaagtatcg tggctatatc cgtttagtgt cgtcggatat    36120
tctgacggtg atgacattaa acactctact gaacaacatt gcctcaactg agttggggat    36180
gtcgtctatt cagtctcttg gtacatcact aggtcgctca gtgcaatcag aaatcatagc    36240
tcagaatgct gaggtggttg cacctgcgta catgaaccga gtgtatgagt acttgaaaga    36300
gcacaagacg cgttcccaat ctcatatctt gcgtacgttc cgtgctgcca gtgcgaacgt    36360
gaaactggaa actgacccctt gggataacac gacctgcttt aacgtaggcc gcttgttgct    36420
ccagtgtgtg cacgacacag gtatctttga gtgggtgcaa ggcccgaaag gtttactata    36480
cgctgagcca gccgaggaac tgcaaggcgt gttctcggat gtccttgagc atgctgacac    36540
tatggtgcac tacccaccga tgattgtccc tccggtacgc catgaagaca tttacaacgg    36600 cggttatttta actgacctca gccgtcgtca cacgtactcg aaccgccaca tcaagcgttc    36660
ccgtttacgt gaagtgaacg aggcgtttaa acaggcgaat ggtatccgcc aagcgttgaa    36720
caaagcacag gaagtacctt atgttgtgaa caaaagtatt tacgacttag tactacaagc    36780
caaggctaca ggctttgacg ttggcattcc tagccaccac cagaaaccac agcctaagtt    36840
ccacttacac ggcactgata aggctgactg gtctgaggat gaccaagagg cgtttgaggt    36900
ttggaagacc cagatgcgtc aatggtacac aaaggaacgc aaacgtgtat ctcagattcg    36960
tcagttggct atcacgcttg acctgtgccg tcgcttcatg gacgaggatg cgctgtactt    37020
cccgacttgc gtggactggc gttaccgctt gtacttcaaa tctcacttga acccacaagg    37080
ctctgacatc caaaaggcgt tgctgctact tgggcgtaag aagccgctag gtaagcgtgg    37140
tctgttctgg ttgaaatccc atgtcgctac gtgctttggc tttgataaac cattgttcga    37200
agaacgtgcc aagtggactg aggaacgcat tgacgcgatt cgtgagtggg tgaaagaccc    37260
attgaacaac gaagacttca aagatgcaga cgagttctgg tgtatgcttg cggctagtat    37320
ccaactaatc gaagcactag actcacctga ccctgagaag tatgagtcaa acattgcggt    37380
tgcattggac gccactaact ctggcggtca acacttctct gcaatgctgc gtgaccctat    37440
cggtggtaag ctaacgaacc tattctggga cgggaactta accaaggccg acctgtacat    37500
```

```
ggatgtgaag cagcgtactg attcgaaaat caaggttgct ctacgtgacc ctgagacaat   37560
cgtgcaagca cattactgga cactgaaccc tatcacacgt tcaatgacca agcgcccaac   37620
gatgacgtac ttttattctg ccacattacg tagctgcacg gattacattt tccttggtgc   37680
tgctgatgag ggctatgagg gtacagatga gtacacgctg ttcaagctgt gttcgttcgt   37740
atcgccgttg atgcgtgaca gtattaatga ggcaatgcca gccgctgcac gtggtatgga   37800
ttacctcaag gctgtgtgtc agcgagtgcc aatggaacat cacttgcagt ggaagacagt   37860
gctcggtggt ctggtgatta accgttactg taaccgccat gagactcgcg ttaaagtgcg   37920
tagcatgggt atcaaccaag tagtgctgta caacttcgac tacgagcgca atcaccgcca   37980
gaaagctgta tccggtatct caccgaactt tattcaccaa ggggatagct cacaccttat   38040
gatgaccatc ttgaactttg acggtgacat catcccaatc cacgattcag ttgcgactca   38100
cgcctgtgac gttgatgacc tgcaccgtgt gttgcgtgag cagttcgtga ttctatacac   38160
tgagcaccag aacccacttg aggttatccg tgacgcagcg ttagaagcag gggctgacct   38220
tgagggtatt gaaatgccac caatgggtac attgaatctg gagctggtta agattcgcc    38280
attcttcttc tgctaattta agtcccacg aacaggagag acacgaagtg tccaattata    38340
ctctagaatt ctacacaggt agaaaggcta tgctaggtgc gcgagttgtc gcaaacctag   38400
cgtaccacaa caaccctgag ttcgctcagg gtattacctc taaagacttt agagattccg   38460
ttgccgactc agttgatggg ttcatgtgta tgggtatcca tcacaaaggc aacttaatag   38520
ggggctgcgc tataacagca ccgtacacga caccgcatat cagtggtaga ggcgtgggcg   38580
ttgtattaag ctacgtgctc ccgaaccaca atatcggaca tcacatgtac cgtgcgatta   38640
tgcgctatgc caaggcacaa cgtctggact gggtgctcat ccctcacaag cagggcgagt   38700
acgagtacga gctcaagtac tacaaggtga acatgggat tcgatagtgg taaaggtgcg    38760
gcgaaagaag cacgccgcca agctgaggcg caaaagaaac agttcgaagc tgaacagact   38820
cgaatgcgtg aggctaacac actccaagct aacaaagctc ttgacgacgt agttaaggtt   38880
gagacaggcg gttctgcaaa cttagcagcc gatgatgctc ttggtcttac aactcgtaaa   38940
cgtaagatgg ctgatgttag ctcaagctta ggattataag gtactgtatg cagactcaag   39000
agactcacga ggctctgttc aaacgatatg aggactctga ggttactctg agttcagagc   39060
gttacgcttt ctggacagtg cctaccgttt ttacacgtga gaacaaagac ggagagcgcg   39120
tatcacttca acgcgacttc caatctcacg gtgctatgtt ggttaacaac cttgctagta   39180
aactgacacg gacgcttttc ccaaccggga tgagcttctt ccgtatctca gacacagata   39240
agatgcgtga aatcattgcg caattgggta gtgagaacgc gcaactttct gctgtgttta   39300
ctggtatcga gcgtgaagca atgacattgc tcaccaccca cgctggtttt gctcagttaa   39360
cccacttaat gaagttactt atcatcactg gtaatgcgtt gctgtaccgc gacccactaa   39420
ccggacgtat gaccgtgtac agtgtacgcg attatgttgt gcgtcgtgac ggtgctggtc   39480
gagtgttgtg cacagttcta cgtgagcgtg tcccagttca ggacgtgcca gaagaattcc   39540
gcccaaccgg gtacacagac cctaccgctg atgtttggtt ataccaag attcaacgcg     39600
agacgcgtga tgctggtgac gttttttgtga ttactcaaca gattgatggt aagcctgttg   39660
gcacacttag tgtttacccct gagaagctat gtccttacat ccctgcggtg tggaacttgg   39720
tttctggtga gcattatggt cgtggccatg tggaagacca tgcaggtgca ttcgcacgtg   39780
tgtcggagct aaacccaagcc ctgactctgt atgagattga agctatgcga gtcgttaacc   39840
tcgtgtcgcc taagagtact gctgacgttg acgcattgaa tgatgctgag actggtgagt   39900
```

```
acgttgcagg tgatggtgag ggtatcaagg cgcatgaagc tggtgaggca cgtaagattg    39960
ctgaggtcgt gaatgaccta cagatggttc ttgcggagct ggcacgagcg ttcatgtaca    40020
ctggtaacgt ccgtgatgct gaacgtgtaa cagcagaaga aatcaagaac aacgttcgtg    40080
aggcagagga aaacatgggt ggcatctacg ctacacttgc tgagattctg catatcccgt    40140
tagcgcacat tctgacagtt gaggctcgac ctgagctgct ggcactgttg caagctaatg    40200
cggttagcct agacattcaa gtaggtactg cggctatcaa ccgtagtatt gtggtgcaac    40260
gtctgggtct agttgcgaac gacattaact tgattctccc tgtacttgca caagctacaa    40320
aacgtaccaa ccccgaccga gtgattgacc taatcctcgc aggtcatggt gttgacccaa    40380
ctgagatttt ctacacagaa caagagctgc aacagctaca agcggctgag aagctgctg     40440 ctcaagcccc tgcctccggt atggcacttg atgctggctc tgctgcgcta ttgtctgaac    40500
agcaaggatt gactcaataa tgcaagatac aaatcttcca ccgggcgtac cagcagcggg    40560
taaacctgct gacgttccga accaaccaca accagcgcag aaccctgcac cacaacctgc    40620
accagccgac gaccctgtac tgggtaatca accacaacct gctgctgctc cacagccaga    40680
acctcaagtt cctgctgaac cggagcaaac agacccagcc gcaggtcaga ttacgttaca    40740
gacaggtgac gccgcagttg atgctggctt acagatgctt gctcaagtat cgggctgtac    40800
cgatgctgac gtagagcgag ctatgggtaa tgcactgcgt tatggtgatg cctctttgat    40860
tgacgagaag ttcctccaag aacgcctcgg caactacgct ggctacgcaa agaccttagc    40920
tgagacgtac ctcgctaacg ctgcttcaaa cactgaacgc actgttaatg aagtacatac    40980
cttagctggt ggtgctgagg cgtgggcaca agcgcgtgat gtgttcatgg cgaacgctcc    41040
tgcgcatatt cagactgcgg tcaagactat ggcaaacagc ggtctagcca aggacgcagc    41100
tcagatggta ttagactacg cccgtcagtc tggtgcttta ccagttcaag gccaacacat    41160
tcatgggatg ggtggtcagg ctggcaacac tgcgttgtct gctgctgagt tctcgaaaga    41220
acttgcggat ttacgtacca agtttggtaa cacttctttt gaaagtggcc ctgctggtca    41280
agcgtatcag aatctgcttg aacgccgcgc acgtggcaaa caactggggc gataagcccc    41340
tttttgcgtt tctgacgcgt aaaattttag actaaatctc tcaaccataa ggattcaaaa    41400
tggctgatac atcatacaaa ccgggcttga ctcgcccaca ctggggtggt gctgcttctg    41460
atgaagatat tcacctagag gtgtaccaaa acgaagttga cactcgtttc cagtacgcag    41520
ctatgttccg tggcttgtct gcgcaacgtt caactgctga acgctctaac acttaccgta    41580
ttgaccgctt gaacacttca acagtaaaag gccgtcgttc cggtgaagct ctggataaca    41640
cgcctgtacg caacgataaa atgattatcg tcgtggacac agtgctgtac atccgtaacc    41700
caatcgacta ccaagacgac tggactgcac ctgacttcct aaccgaaatg ggtcagaaca    41760
acggctctga gttcgctgag gtctttgacc aagcgcacct tatccagctc atcaaggtc     41820 gtgcttggga tgcaccagaa cacttgaaac ctgcgttcaa ggacggtgtg gaagtgctgg    41880
caacttacaa gactgctgcg gttgctcagg aagaacttga ggcgaacgct atctctatca    41940
acgaagctca caaggctggt gtgactgagc tagtgaagcg taaagttcca ctgactgacc    42000
aaatcactct tgtgtcacca gacatttact ctgcgctagt agagcatcca aaactgctga    42060
accaagagtt caacgttgat atgtctgact acggtggtcg tcgtgtcgtt cgtatgaacg    42120
gtgtaccagt agttgagtgt accgagttcc caactggtgc aatcaatgct cacccacttg    42180
gcactgcatt caacgtatct gcggaagatg cgaaatgtca aatggttact ttctctaaat    42240
```

-continued

```
ctcgtacgct tgtgactgtg gaagcacacc cattcacaac tcgtatctgg gatgacgaga    42300
aagagttctg taacgtactt gactgttacg ctatgtacac agttggtcag cgtcgcccag    42360
acactgcaat cgttactaag ttcgaagaac cagcataagg agtagatgaa tggctaaagt    42420
aatcgaccta cgcgctaagt ggacaccaga cgaagcgcgt caaaagcaga agcgtaacgc    42480
tcgtcagaac aaacctgtag ctgctggtac gccagagaaa acagagactg agagctaatc    42540
agcaataata cccaagggga gtggcttcgg ctgctcccct tttttgtttg gagtgcttaa    42600
aatatgacct tactagatgc aatcaatatc tcgttgactg cgattggtga gtaccgcatc    42660
acatccgaca ctgttcgcaa ccctaccatt ggtatcgtca aggacactct tgaaactaaa    42720
cgcaaactat tgctgagcga tggttggtgg ttcaacgagc gtgaaatgac gttgtaccct    42780
gatgtcgagg ggcatatcta tctaccga                                       42808
```

VIBRIO PARAHAEMOLYTICUS BACTERIOPHAGE VIB-PAP-1 AND USE THEREOF FOR INHIBITING PROLIFERATION OF VIBRIO PARAHAEMOLYTICUS

CROSS-REFERENCE TO RELATED APPLICATIONS

This application is a U.S. National Phase Application of International Application No. PCT/KR2016/012904, filed Nov. 10, 2016, which claims priority to Korean Application No. 10-2015-0182590, filed Dec. 21, 2015, each of which are hereby incorporated by reference in their entirety.

REFERENCE TO SEQUENCE LISTING

The Sequence Listing submitted Jul. 5, 2018 as a text file named "08162_0042U1_Revised_Sequence_Listing.txt," created on Jun. 29, 2018, and having a size of 56,314 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Vibrio parahaemolyticus* cells, and a method for preventing and treating the infections of *Vibrio parahaemolyticus* using a composition comprising the bacteriophage as an active ingredient. More particularly, the present invention relates to a Podoviridae bacteriophage Vib-PAP-1 (Accession NO: KCTC 12817BP) that is isolated from the nature and can kill *Vibrio parahaemolyticus* cells specifically, which has a genome represented by the nucleotide sequence of SEQ. ID. NO: 1, and a method for preventing the infections of *Vibrio parahaemolyticus* and thereafter treating them using the composition comprising said bacteriophage as an active ingredient.

2. Description of the Related Art

*Vibrio parahaemolyticus* is a Gram-negative bacillus belonging to the genus *Vibrio* and gives rise to acute food poisoning and enteritis in human and vibriosis in fish. There are a variety of symptoms by the vibriosis in fish. The infected fish may manifest darkened body color and skin ulcer and sometimes reveal reddening of rostrum and skin flare. Also, in terms of anatomical signs, bleeding or congestion of liver is observed.

The outbreak of vibriosis caused by the infection of *Vibrio parahaemolyticus* occurs frequently, thereby results in economical damages a lot. Therefore, it is required to develop a novel procedure for preventing and further, treating the infections of *Vibrio parahaemolyticus*.

The fish aquaculture industry continues to develop rapidly every year, because it makes food resources acquired easily when being insufficient in the wild fish capture. However, as the aquaculture industry develops increasingly, environmental pollution caused by feeds increase around aquafarms. Particularly, a lot of antibiotics included in the feeds are spread widely to rather threaten human health. In the aquafarms, chemotherapeutic antibiotics are utilized in an excessive amount to eradicate bacterial diseases practically. As a consequence, multi-drugs resistant bacterial strains are emerging frequently, which leads to economical losses in the aquafarms. Moreover, such an abuse of antibiotics without any restraint can threaten national health and thereby influence mentally upon nations to reduce consumption of fish, resulting in weakning overall competition of the fish aquaculture industry. Therefore, it is urgently requested to develop a novel method for preventing bacterial infections and thereafter treating them effectively. Especially, the safety of sea food becomes a main social concern and thus, environmental-friendly methods are preferred.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After proliferation, the progenies destroy the bacterial cell wall to escape from the host, suggesting that the bacteriophage has the killing ability of bacteria. The bacteriophage infection is characterized by its high specificity, so that a certain bacteriophage infects only a specific bacterium. That is, the bacterium that can be infected by certain bacteriophage is limited, suggesting that bacteriophage can kill only a specific bacterium and cannot harm other bacteria. Due to this cell specificity, the bacteriophage confers antibacterial effects upon target bacteria and excludes commensal bacteria in environmental or the intestines of fish. Meanwhile, conventional antibiotics affect various kinds of bacteria coincidently. However, the use of bacteriophages does not disturb normal microflora either in the intestines of fish, because of killing the target bacteria selectively. Hence, the bacteriophage may be utilized safely and thus lessen the probability of adverse actions, compared to any other antibiotics.

Bacteriophage was first found out by an English bacteriologist Twort in 1915 when he noticed that Micrococcus colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new antibacterial agent that can replace the conventional antibiotics. Furthermore, the recent regulation of using antibiotics is fortified by the government world-widely. The interest on bacteriophages is increasing more and also industrial applications are increasingly achieved.

As demonstrated above, bacteriophages tend to be highly specific for bacteria. The specificity often makes bacteriophages effective upon a part of bacteria, even though belonging to the same kinds. In addition, the effectiveness of bacteriophage is different, depending upon target bacterial strains. Therefore, it is necessary to collect many kinds of bacteriophages that are useful to control specified bacteria efficiently. Hence, in order to develop a use of bacteriophages for coping with *Vibrio parahaemolyticus*, a lot of bacteriophages (many kinds of bacteriophages that give an antibacterial action against *Vibrio parahaemolyticus*) should be acquired. Furthermore, the resulting bacteriophages need to be screened whether or not superior to others in respects of antibacterial strength and spectrum.

Therefore, the present inventors tried to develop a composition applicable for the prevention or treatment of *Vibrio parahaemolyticus* infections by using a bacteriophage that is isolated from the nature and can kill *Vibrio parahaemolyticus* cells selectively, and further to establish a method for preventing or treating the infections of *Vibrio parahaemolyticus* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used to prevent and treat the infections of *Vibrio parahaemolyticus*, leading to the completion of the present invention.

SUMMARY OF THE INVENTION

It is an object of the present invention to provide a Podoviridae bacteriophage Vib-PAP-1 (Accession NO: KCTC 12817BP, deposited under the Budapest Treaty on the International Procedure at the Korean Collection for Type Cultures, Korea Research Institute of Bioscience and Biotechnology (KRIBB), 125 Gwahak-ro, Yuseong-gu, Daijeon 305-806, Republic of Korea; the deposit was made on May 20, 2015) that is isolated from the nature and can kill *Vibrio parahaemolyticus* cells specifically, which has the genome represented by the nucleotide sequence of SEQ. ID. NO: 1.

It is another object of the present invention to provide a composition applicable for the prevention of *Vibrio parahaemolyticus* infections, which comprises the bacteriophage Vib-PAP-1 that can infect and kill *Vibrio parahaemolyticus* cells, as an active ingredient and a method for preventing the infections of *Vibrio parahaemolyticus* using said composition.

It is another object of the present invention to provide a composition applicable for the treatment of *Vibrio parahaemolyticus* infections, which comprises the bacteriophage Vib-PAP-1 that can infect and kill *Vibrio parahaemolyticus* cells, as an active ingredient and a method for treating the infections of *Vibrio parahaemolyticus* using said composition.

It is another object of the present invention to provide an immersion agent (medicine bath agent) for preventing and treating the infections of *Vibrio parahaemolyticus* using said composition.

It is also an object of the present invention to provide a feed additive effective upon farming by preventing and treating the infections of *Vibrio parahaemolyticus* using said composition.

To achieve the above objects, the present invention provides a Podoviridae bacteriophage Vib-PAP-1 (Accession NO: KCTC 12817BP) that is isolated from the nature and can kill specifically *Vibrio parahaemolyticus* cells, which has the genome represented by the nucleotide sequence of SEQ. ID. NO: 1, and a method for preventing and treating the infections of *Vibrio parahaemolyticus* using a composition comprising the bacteriophage as an active ingredient.

The bacteriophage Vib-PAP-1 has been isolated by the present inventors and then deposited at Korean Collection for Type Cultures, Korea Research Institute of Bioscience and Biotechnology in May 20, 2015 (Accession NO: KCTC 12817BP).

In addition, the present invention also provides an immersion agent and a feed additive applicable for the prevention or treatment of *Vibrio parahaemolyticus* infections, which comprises the bacteriophage Vib-PAP-1 as an active ingredient.

Since the bacteriophage Vib-PAP-1 included in the composition of the present invention kills *Vibrio parahaemolyticus* cells efficiently, it is regarded effective to prevent or treat vibriosis (infections) caused by *Vibrio parahaemolyticus*. Therefore, the composition of the present invention can be utilized for the prevention and treatment of vibriosis caused by *Vibrio parahaemolyticus*, but not limited thereto.

In this description, the term "prevention" or "prevent" indicates (i) to block the infections of *Vibrio parahaemolyticus*; and (ii) to block the development of diseases caused by *Vibrio parahaemolyticus*.

In this description, the term "treatment" or "treat" indicates (i) to suppress the vibriosis caused by *Vibrio parahaemolyticus*; and (ii) to relieve the vibriosis caused by *Vibrio parahaemolyticus*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Vib-PAP-1 is included as an active ingredient. At this time, the bacteriophage Vib-PAP-1 is included at the concentration of $1\times10^1$ pfu/ml~$1\times10^{30}$ pfu/ml or $1\times10^1$ pfu/g~$1\times10^{30}$ pfu/g, and preferably at the concentration of $1\times10^4$ pfu/ml~$1\times10^{15}$ pfu/ml or $1\times10^4$ pfu/g~$1\times10^{15}$ pfu/g.

The composition of the present invention can be formulated by the methods that can be performed by those in the art by using a pharmaceutically acceptable carriers and/or excipients in the form of unit dose or in a multi-dose container. The formulation can be in the form of solution, suspension or emulsion in oil or water-soluble medium, extract, powder, granule, tablet or capsule. At this time, a dispersing agent or stabilizer can be additionally included.

The composition of the present invention can be prepared as an immersion agent or a feed additive according to the purpose of use, but not always limited thereto.

For this purpose, other bacteriophages that can confer an antibacterial activity against other bacterial species can be further comprised in the composition of the present invention in order to improve its effectiveness.

In addition, other kinds of bacteriophages that have an antibacterial activity against *Vibrio parahaemolyticus* can be further comprised in the composition of the present invention. Besides, these bacteriophages can be combined properly so as to maximize antibacterial effects, because their antibacterial activities against *Vibrio parahaemolyticus* can be differential in respects of antibacterial strength and spectrum.

Advantageous Effect

The method for preventing and treating the infections of *Vibrio parahaemolyticus* using this composition comprising the bacteriophage Vib-PAP-1 as an active ingredient, has the advantage of high specificity for *Vibrio parahaemolyticus*, compared with the conventional methods based on the chemical materials including the conventional antibiotics. That means, the composition of the present invention can be used for preventing or treating the infections of *Vibrio parahaemolyticus* specifically without affecting normal microflora, and accordingly has fewer side effects. In general, when chemical materials such as antibiotics are used, commensal bacteria are also damaged to weaken immunity in animals with carrying various side effects. In the meantime, the composition of the present invention uses the bacteriophage isolated from the nature as an active ingredient, so that it is very nature-friendly.

Besides, the antibacterial activity of bacteriophages against target bacteria is different, even if belonging to the same species, in respects of antibacterial strength and spectrum (within several strains of *Vibrio parahaemolyticus*, the antibacterial range of bacteriophages contributing to every strain. Typically, bacteriophages are usually effective upon a part of bacterial strains even in the same species. That is to say, the antibacterial activity of bacteriophage is different depending on bacterial strain in spite of belonging to the same species). Then, the bacteriophage of the present invention can provide antibiotic activity against *Vibrio parahaemolyticus* different to that provided by other bacteriophages acting on *Vibrio parahaemolyticus*. Therefore, the bacteriophage of the present invention can provide different applicability for fish aquaculture industry.

BRIEF DESCRIPTION OF THE DRAWINGS

The application of the preferred embodiments of the present invention is best understood with reference to the accompanying drawings, wherein:

FIG. 1 is an electron micrograph showing the morphology of the bacteriophage Vib-PAP-1.

FIG. 2 is a photograph illustrating the capability of the bacteriophage Vib-PAP-1 to kill *Vibrio parahaemolyticus* cells. The clear zone on the dish is the formation of plaque by lysis of target bacteria cells.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Bacteriophage Capable of Killing *Vibrio parahaemolyticus*

Samples were collected from the nature to screen the bacteriophage capable of killing *Vibrio parahaemolyticus*. In the meantime, the *Vibrio parahaemolyticus* strain used for the bacteriophage isolation herein was obtained from Korean Collection of Type Cultures, Korea Research Institute of Bioscience and Biotechnology (Accession NO: KCTC 2729).

The isolation procedure of the bacteriophage is described in detail hereinafter. The collected sample was added to LB (Luria-Bertani; tryptone, 10 g/L; yeast extract, 5 g/L; sodium chloride, 10 g/L) broth inoculated with *Vibrio parahaemolyticus* at the ratio of 1/1,000, followed by shaking culture at 37° C. for 3~4 hours. Upon completion of the culture, centrifugation was performed at 8,000 rpm for 20 minutes and supernatant was recovered. The recovered supernatant was inoculated with *Vibrio parahaemolyticus* at the ratio of 1/1,000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing *Vibrio parahaemolyticus* was included therein.

Spot assay was performed as follows; LB broth was inoculated with *Vibrio parahaemolyticus* at the ratio of 1/1,000, followed by shaking culture at 37° C. for overnight. 3 ml (1.5 of $OD_{600}$) of the culture broth of *Vibrio parahaemolyticus* prepared above was spread on LA (Luria-Bertani Agar; tryptone, 10 g/L; yeast extract, 5 g/L; sodium chloride, 10 g/L; agar, 15 g/L) plate. The plate stood in a chamber for about 30 minutes to dry. After drying, 10 μl of the resulting filtrate was spotted directly onto the surface of the *Vibrio parahaemolyticus* lawns and dried for about 30 minutes. Following drying, the plate was incubated at 37° C. for a day and then, examined for the formation of clear zone on the surface of the bacterial lawns. If a clear zone was generated where the filtrate was dropped, it is judged that the bacteriophage capable of killing *Vibrio parahaemolyticus* should be included in the filtrate. Through the above procedure, the filtrate containing the bacteriophage having the killing ability of *Vibrio parahaemolyticus* can be obtained.

After that, the bacteriophage was isolated from the filtrate confirmed above to have the bacteriophage capable of killing *Vibrio parahaemolyticus*. The conventional plaque assay was used for the isolation of pure bacteriophage. In detail, a plaque formed in the course of the plaque assay was picked up by using a sterilized tip, which was then added to the culture solution of *Vibrio parahaemolyticus*, followed by culturing at 37° C. for 4~5 hours. Upon completion of the culture, centrifugation was performed at 8,000 rpm for 20 minutes to obtain supernatant. The recovered supernatant was inoculated with *Vibrio parahaemolyticus* culture at the ratio of 1/50, followed by culturing at 37° C. for 4~5 hours. To increase the titer of the bacteriophage, the above procedure was repeated at least 5 times. Then, centrifugation was performed at 8,000 rpm for 20 minutes to obtain supernatant. Plaque assay was performed by using the resulting supernatant. In general, the pure bacteriophage isolation is not completed by one-time procedure, so the above procedure was repeated by using the resulting plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by electron microscopy. Until the pure bacteriophage isolation was confirmed by electron microscopy, the above procedure was repeated. The electron microscopy was performed by the conventional method. Briefly, the solution containing the pure bacteriophage was loaded on copper grid, followed by negative staining with 2% uranyl acetate. After drying thereof, the morphology was observed using a transmission electron microscope. The electron micrograph of the bacteriophage isolated in the present invention is presented in FIG. 1. Based on the morphological characteristics, the bacteriophage isolated above was confirmed as belonging to the family Podoviridae.

The solution containing the pure bacteriophage confirmed above proceeded to purification. The culture broth of *Vibrio parahaemolyticus* was added to the solution containing the pure bacteriophage at the volume of ⅟₅₀ of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 µm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was suspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Vib-PAP-1 and then deposited at Korean Collection for Type Cultures, Korea Research Institute of Bioscience and Biotechnology in May 20, 2015 (Accession NO: KCTC 12817BP).

Example 2

Separation and Sequence Analysis of the Bacteriophage Vib-PAP-1 Genome

The genome of the bacteriophage Vib-PAP-1 was separated as follows. The genome was separated from the bacteriophage suspension obtained in Example 1. First, in order to eliminate DNA and RNA of *Vibrio parahaemolyticus* cells included in the suspension, DNase I and RNase A were added 200 U each to 10 ml of the bacteriophage suspension, which was incubated at 37° C. for 30 minutes. 30 minutes later, to remove the DNase I and RNase A activity, 500 µl of 0.5 M ethylenediaminetetraacetic acid (EDTA) was added thereto, which was incubated for 10 minutes. The suspension was further incubated at 65° C. for 10 minutes and then added with 100 µl of proteinase K (20 mg/ml) to break the outer wall of the bacteriophage, followed by incubation at 37° C. for 20 minutes. After that, 500 µl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 µl of water. This procedure was repeated to obtain a sufficient amount of the bacteriophage Vib-PAP-1 genome.

The nucleotide sequence of the bacteriophage Vib-PAP-1 genome obtained above was determined by Next Generation Sequencing analysis using Roche 454 GS Junior device. As a result, it is suggested that the final genome of bacteriophage Vib-PAP-1 has 42,808 bp of size and the nucleotide sequence of the whole genome has SEQ. ID. NO: 1.

Similarity of the genomic sequence of the bacteriophage Vib-PAP-1 obtained above with the previously reported bacteriophage genome sequences was investigated by using BLAST. From the BLAST result, it is demonstrated that the genomic sequence of bacteriophage Vib-PAP-1 has a relatively high homology with the genomic sequence of *Vibrio bacteriophage VP*93 (Genbank Accession NO: FJ896200.1) (Query coverage/identity: 99%/95%). Nevertheless, the bacteriophage Vib-PAP-1 has a circular genome while the *Vibrio bacteriophage VP*93 has a linear genome. Thus, it is determined that they should be different kinds of bacteriophages. In addition, the genomic sequence of bacteriophage Vib-PAP-1 was compared to that of *Vibrio bacteriophage VP*93 by using NEBcutter V2.0 Web program. As a result, it is illustrated that the bacteriophage Vib-PAP-1 genome can be digested in a single cut by 15 kinds of restriction enzymes (AnaI, AvrII, BmtI, BseRI, BsoBI, BssHII, BstNI, BstZ17I, MscI, NheI, NruI, PspGI, PvuII, SalI, XbaI), while the *Vibrio* bacteriophage VP93 can be singly cut by 10 kinds (AcuI, AfeI, BmtI, BseRI, BssHII, EarI, MscI, NheI, NsiI, Pf1MI). Therefore, it is clarified again that they should be different kinds of bacteriophages.

Based upon this result, it is concluded that the bacteriophage Vib-PAP-1 should be a novel bacteriophage not reported previously. Either, it is referred that when bacteriophages are different in their kinds, their antibacterial strength and spectrum become different typically. As a consequence, it is confirmed that the bacteriophage Vib-PAP-1 provides have more remarkable antibacterial activity than any other bacteriophages aforementioned.

Example 3

Investigation of Killing Ability of the Bacteriophage Vib-PAP-1 Against *Vibrio parahaemolyticus*

The killing ability of the isolated bacteriophage Vib-PAP-1 against *Vibrio parahaemolyticus* was investigated. To do so, the formation of clear zone was observed by the spot assay by the same manner as described in Example 1. The *Vibrio parahaemolyticus* used for this investigation were total 17 strains which had been isolated and identified as *Vibrio parahaemolyticus* previously by the present inventors. The bacteriophage Vib-PAP-1 demonstrated the killing ability against 15 strains of *Vibrio parahaemolyticus* used in this experiment. The representative result of the killing ability test is shown in FIG. 2. In the meantime, the activity of the bacteriophage Vib-PAP-1 to kill *Edwardsiella tarda, Vibrio anguillarum, Vibrio ichthyoenteri, Lactococcus garvieae, Streptococcus parauberis, Streptococcus iniae* and *Aeromonas salmonicida* was also investigated respectively. As a result, it is concluded that the bacteriophage Vib-PAP-1 does not have the killing activity against these microorganisms.

Therefore, it is confirmed that the bacteriophage Vib-PAP-1 has the specific ability to kill *Vibrio parahaemolyticus* cells and a broad antibacterial spectrum against *Vibrio parahaemolyticus*, suggesting that the bacteriophage Vib-PAP-1 of the present invention can be used as an active ingredient of the composition for preventing and treating the infections of *Vibrio parahaemolyticus*.

Example 4

Preventive Effect of Bacteriophage Vib-PAP-1 on the Infections of *Vibrio parahaemolyticus*

100 μl of the bacteriophage Vib-PAP-1 solution at $1 \times 10^8$ pfu/ml was added to a tube containing 9 ml of LB broth. To another tube containing 9 ml of LB broth, the same amount of LB broth was further added. *Vibrio parahaemolyticus* culture solution was added to each tube until $OD_{600}$ reached about 0.5. Then, the tubes were transferred to a 37° C. incubator, followed by shaking-culture, during which the growth of *Vibrio parahaemolyticus* was observed. As presented in Table 1, the growth of *Vibrio parahaemolyticus* was inhibited in the tube adding the bacteriophage Vib-PAP-1 solution, while the growth of *Vibrio parahaemolyticus* was not inhibited in the tube without adding the bacteriophage solution.

TABLE 1

Growth inhibition of *Vibrio parahaemolyticus*

| Treatment | $OD_{600}$ | | |
|---|---|---|---|
| | 0 min. | 60 min. | 120 min. |
| −bacteriophage solution | 0.496 | 1.233 | 2.135 |
| +bacteriophage solution | 0.496 | 0.286 | 0.122 |

The above results indicate that the bacteriophage Vib-PAP-1 should not only inhibit the growth of *Vibrio parahaemolyticus* but also can kill *Vibrio parahaemolyticus*. Therefore, it is concluded that the bacteriophage Vib-PAP-1 can be used as an active ingredient of the composition in order to prevent the infections of *Vibrio parahaemolyticus*.

Example 5

Preventive Effect of Bacteriophage Vib-PAP-on the Infections of *Vibrio parahaemolyticus* in Animal Model Preventive effect of the bacteriophage Vib-PAP-1 on sea basses suffered from *Vibrio parahaemolyticus* infection was investigated. Particularly, total 2 groups of juvenile sea bass (50 juvenile sea basses per group; body weight 5~7 g, body length 8~10 cm) were prepared, which were cultured separately in different water tanks for 14 days. Surrounding environment of the water tanks was controlled. The temperature and humidity in the laboratory where the water tanks stayed were also controlled. From the $1^{st}$ day of the experiment, sea basses of the experimental groups (adding the bacteriophage) were fed with feeds adding the bacteriophage Vib-PAP-1 at $1 \times 10^8$ pfu/g according to the conventional feed supply procedure, while sea basses of the control group (without adding the bacteriophage) were fed with the same feed without adding the bacteriophage according to the conventional procedure. From the $7^{th}$ day of the experiment, the feeds of both groups were contaminated with *Vibrio parahaemolyticus* at $1 \times 10^8$ pfu/g for 2 days and thereafter provided respectively twice a day so as to bring about the infections of *Vibrio parahaemolyticus*. From the next day of inducing such an infection for 2 days (the $9^{th}$ day of the experiment), the feeds without contaminated *Vibrio parahaemolyticus* were provided again respectively for both the groups. Then, all the test animals were examined whether being suffered from *Vibrio parahaemolyticus* infection or not. The outbreak of infectious disease caused by *Vibrio parahaemolyticus* was detected by measuring a body darkening index. The measurement of body darkening index was performed by the conventional method obtaining Dark Coloration (DC) score (0: normal, 1: light coloration, 2: dark coloration). The results are shown in Table 2.

TABLE 2

Dark coloration score (average values)

| | Days | | | | | |
|---|---|---|---|---|---|---|
| | D9 | D10 | D11 | D12 | D13 | D14 |
| Control group (−bacteriophage) | 0.68 | 0.68 | 0.72 | 0.84 | 1.04 | 1.08 |
| Experimental group (+bacteriophage) | 0.12 | 0 | 0 | 0 | 0 | 0. |

From the above results, it is confirmed that the bacteriophage Vib-PAP-1 of the present invention could be very effective to prevent infectious diseases caused by *Vibrio parahaemolyticus*.

Example 6

Therapeutic Effect of Bacteriophage Vib-PAP-1 on the Infections of *Vibrio parahaemolyticus*

Therapeutic effect of the bacteriophage Vib-PAP-1 on sea basses suffered from *Vibrio parahaemolyticus* infection was investigated. Particularly, total 2 groups of juvenile sea bass (60 juvenile sea basses per group; body weight 5~7 g, body length 8~10 cm) were prepared, which were cultured separately in different water tanks for 14 days. Surrounding environment of the water tanks was controlled. The temperature and humidity in the laboratory where the water tanks stayed were also controlled. From the $5^{th}$ day of the experiment, feeds adding *Vibrio parahaemolyticus* cells at $1 \times 10^8$ cfu/g were provided twice a day for 3 days according to the conventional feed supply procedure. Sea bass subjects showing clinical symptoms of infectious disease caused by *Vibrio parahaemolyticus* from the last day of this procedure, were observed in both water tanks. From the next day of providing feeds adding *Vibrio parahaemolyticus* cells for 3 days (the $8^{th}$ day of the experiment), sea basses of the experimental groups (adding the bacteriophage) were fed with feeds adding the bacteriophage Vib-PAP-1 at $1 \times 10^8$ pfu/g according to the conventional feed supply procedure, while sea basses of the control group (without the bacteriophage) were fed with the same feeds without adding the bacteriophage Vib-PAP-1 according to the conventional procedure. After the 8$^{th}$ day of the experiment, all the test animals were examined whether being suffered from infectious disease caused by *Vibrio parahaemolyticus* or not. The outbreak of infectious disease caused by *Vibrio parahaemolyticus* was detected by measuring body darkening index. The measurement of body darkening index was performed by the conventional method obtaining Dark Coloration (DC) score (0: normal, 1: light coloration, 2: dark coloration). The results are shown in Table 3.

TABLE 3

| | Dark coloration score (average values) | | | | | | |
|---|---|---|---|---|---|---|---|
| Days | D 8 | D 9 | D 10 | D 11 | D 12 | D 13 | D 14 |
| Control group (−bacteriophage) | 0.97 | 1.03 | 1.10 | 1.17 | 1.17 | 1.23 | 1.27 |
| Experimental group (+bacteriophage) | 1.00 | 0.93 | 0.87 | 0.77 | 0.43 | 0.20 | 0.13 |

From the above results, it is confirmed that the bacteriophage Vib-PAP-1 of the present invention could be very effective to treat the infectious disease caused by *Vibrio parahaemolyticus*.

Example 7

Preparation of Feed Additives and Feeds

Feed additives were prepared by adding the bacteriophage Vib-PAP-1 solution at the concentration of 1×10$^8$ pfu/g feed additives. The preparation method thereof was as follows: Maltodextrin (50%, w/v) was added to the bacteriophage solution, mixed and then resulting mixture was freeze-dried. Lastly, the dried mixture was grinded into fine powders. The drying procedure above can be replaced with drying under a reduced pressure, drying at warm temperature, or drying at room temperature. To prepare the control for comparison, feed additives that did not contain the bacteriophage but contained only buffer (10 mM Tris-HCl, 10 mM MgSO$_4$, 0.1% Gelatin, pH 8.0) were prepared.

The above two kinds of feed additives were mixed with raw fish-based moist pellet at the volume of 250 times the volume of additives, resulting in two kinds of final feed additives.

Example 8

Preparation of an Immersion Agent (Medicine Bath Agent)

An immersion agent comprising 1×10$^8$ pfu/ml of bacteriophage Vib-PAP-1 was prepared. The preparation method was as follows: 1×10$^8$ pfu of the bacteriophage Vib-PAP-1 was added to 1 ml of buffer, which was well mixed. To prepare the control, the buffer itself that is the same with the one used for the mixture of the bacteriophage solution was prepared.

The prepared two kinds of immersion agents were diluted with water at the ratio of 1:1,000, resulting in the final immersion agents for the experiment.

Example 9

Effect on Sea Bass Aquafarming

The effect of the feeds and the immersion agents prepared in Example 7 and Example 8 on sea bass aquafarming was investigated. Particularly, the investigation was focused on the mortality. Total 500 juvenile sea basses (body weight 5~7 g, body length 8~10 cm) were grouped into two, 250 sea basses for each group, which proceeded to the following experiment (group A; fed with feed, group B; treated with immersion agent). Each group was divided to two sub-groups again, group of 125 sea basses each (sub-group-①: treated with the bacteriophage Vib-PAP-1, sub-group-②: not-treated with the bacteriophage Vib-PAP-1). Each sub-group sea bass were aquacultured in separate water tanks placed at a certain space interval. Each sub-group was distinguished and named as shown in Table 4.

TABLE 4

| | Sub-groups of sea bass in aquafarming experiment | |
|---|---|---|
| | Sub-group | |
| Treatment | Treated with the bacteriophage Vib-PAP-1 | Not-treated with the bacteriophage |
| Fed with feed | A-① | A-② |
| Treated with immersion agent | B-① | B-② |

Feeds were provided according to the conventional feed supply procedure as presented in Table 4 with the feeds prepared as described in Example 7. The treatment of immersion agent was also performed by the conventional procedure as presented in Table 4 with the immersion agent prepared as described in Example 8. The test result is shown in Table 5.

TABLE 5

| | Mortality of sea bass in aquafarming | |
|---|---|---|
| Group | Dead fish/total test fish (No.) | Mortality (%) |
| A-① | 4/125 | 3.2 |
| A-② | 27/125 | 21.6 |
| B-① | 7/125 | 5.6 |
| B-② | 39/125 | 31.2 |

The above results indicate that the feeds prepared by the present invention and the immersion agent prepared according to the present invention are effective to reduce the mortality of the cultured sea basses. Therefore, it is concluded that the composition of the present invention could be efficiently applied to improve outcomes of sea bass aquaculture.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating an infectious disease caused by *Vibrio parahaemolyticus*, which comprises a step of administering to a subject a composition comprising a Podoviridae bacteriophage Vib-PAP-1 (Accession NO: KCTC 12817BP) that is isolated from nature and can kill *Vibrio parahaemolyticus* cells specifically, wherein the Podoviridae bacteriophage Vib-PAP-1 comprises a genome represented by the nucleotide sequence of SEQ ID NO:1, as an active ingredient.

2. The method for preventing or treating an infectious disease caused by *Vibrio parahaemolyticus* according to claim 1, wherein said composition is administered to a subject in the form of an immersion agent or a feed additive.

* * * * *